United States Patent
Higashitsutsumi et al.

(10) Patent No.: US 9,646,378 B2
(45) Date of Patent: May 9, 2017

(54) INFORMATION PROCESSING APPARATUS, INFORMATION PROCESSING METHOD, PROGRAM, AND MEASURING SYSTEM

(71) Applicant: SONY CORPORATION, Tokyo (JP)

(72) Inventors: Yoshihito Higashitsutsumi, Kanagawa (JP); Jun Iwama, Tokyo (JP); Naoki Nishi, Kanagawa (JP); Yoshiteru Kamatani, Kanagawa (JP); Akinori Kadota, Kanagawa (JP)

(73) Assignee: Sony Corporation, Tokyo (JP)

( * ) Notice: Subject to any disclaimer, the term of this patent is extended or adjusted under 35 U.S.C. 154(b) by 30 days.

(21) Appl. No.: 14/427,757

(22) PCT Filed: Sep. 13, 2013

(86) PCT No.: PCT/JP2013/005447
§ 371 (c)(1),
(2) Date: Mar. 12, 2015

(87) PCT Pub. No.: WO2014/045558
PCT Pub. Date: Mar. 27, 2014

(65) Prior Publication Data
US 2015/0235359 A1      Aug. 20, 2015

(30) Foreign Application Priority Data
Sep. 20, 2012   (JP) ................. 2012-206838

(51) Int. Cl.
*G06K 9/00* (2006.01)
*G06T 7/00* (2017.01)
(Continued)

(52) U.S. Cl.
CPC .............. *G06T 7/0012* (2013.01); *G06K 9/52* (2013.01); *G06K 9/6215* (2013.01); *G06T 1/60* (2013.01); *G06T 7/0042* (2013.01)

(58) Field of Classification Search
USPC ........ 382/100, 103, 106–107, 108, 118, 128, 382/133, 154–155, 162, 168, 173, 181,
(Continued)

(56) References Cited

U.S. PATENT DOCUMENTS

| | | |
|---|---|---|
| 5,755,725 A | 5/1998 | Druais |
| 2006/0092315 A1* | 5/2006 | Payonk ................ A61B 5/0071 |
| | | 348/370 |

(Continued)

FOREIGN PATENT DOCUMENTS

| | | |
|---|---|---|
| JP | 2002-224049 | 8/2002 |
| JP | 2005-065812 | 3/2005 |

(Continued)

OTHER PUBLICATIONS

Official Action (no English translation available) for Japanese Patent Application No. 2012-206838 mailed Aug. 4, 2016, 6 pages.
(Continued)

*Primary Examiner* — Seyed Azarian
(74) *Attorney, Agent, or Firm* — Sheridan Ross P.C.

(57) ABSTRACT

There is provided an imaging unit comprising at least one image sensor, a measuring instrument including at least one marker, a position computing unit, a determining unit, and an output controller, wherein the imaging unit is configured to acquire an image comprising a user and the marker, and provide the acquired image to the position computing unit, wherein the position computing unit is configured to compute a position of the marker with respect to the user based on the image provided by the imaging unit, and further provide the computed position to the determining unit, wherein the determining unit is configured to determine whether the computed position of the marker matches a retrieved measurement position, and further output the result of the determination to the output controller, and wherein the
(Continued)

output controller is configured to provide an indication when the marker position matches the measurement position.

13 Claims, 14 Drawing Sheets

(51) Int. Cl.
*G06K 9/62* (2006.01)
*G06T 1/60* (2006.01)
*G06K 9/52* (2006.01)
*A61B 6/00* (2006.01)

(58) Field of Classification Search
USPC ....... 382/189–190, 199, 209, 219, 232, 254, 382/274, 276, 285–294, 305, 312; 600/476; 424/1.11; 348/370
See application file for complete search history.

(56) References Cited

U.S. PATENT DOCUMENTS

| | | | |
|---|---|---|---|
| 2009/0220415 A1* | 9/2009 | Shachaf | A61B 5/0071 424/1.11 |
| 2009/0326383 A1* | 12/2009 | Barnes | A61B 5/0059 600/476 |
| 2010/0049037 A1 | 2/2010 | Pinter et al. | |
| 2011/0144451 A1 | 6/2011 | Robertson | |
| 2012/0008838 A1* | 1/2012 | Guyon | G06F 19/345 382/128 |

FOREIGN PATENT DOCUMENTS

| | | |
|---|---|---|
| JP | 2005-143890 | 6/2005 |
| JP | 2008-305261 | 12/2008 |
| JP | 2010-264276 | 11/2010 |
| JP | 2010 284239 A | 12/2010 |
| WO | WO 2006/049192 | 5/2006 |
| WO | WO 2009/141769 A1 | 11/2009 |
| WO | WO 2010/102197 A2 | 9/2010 |
| WO | WO 2012/111012 A1 | 8/2012 |

OTHER PUBLICATIONS

Official Action (with English translation) for Chinese Patent Application No. 201380047763.5 dated Jul. 5, 2016, 31 pages.
International Search Report prepared by the European Patent Office on Dec. 13, 2013, for International Application No. PCT/JP2013/005447.
Official Action (no English translation available) for Japanese Patent Application No. 2012-206838 mailed Feb. 4, 2016, 4 pages.
Official Action (with English translation) for Japanese Patent Application No. 2012-206838 mailed Nov. 22, 2016, 4 pages.

* cited by examiner

INFORMATION PROCESSING APPARATUS, INFORMATION PROCESSING METHOD, PROGRAM, AND MEASURING SYSTEM

CROSS REFERENCE TO RELATED APPLICATIONS

This application is a national stage application under 35 U.S.C. 371 and claims the benefit of PCT Application No. PCT/JP2013/005447 having an international filing data of Sep. 13, 2013, which designated the United States, which PCT application claimed the benefit of Japanese Patent Application No. 2013-206838 filed Sep. 20 2012, the disclosures of each of which are incorporated herein by reference.

TECHNICAL FIELD

The present disclosure relates to an information processing apparatus, an information processing method, a program, and a measuring system, and more particularly, to an information processing apparatus, an information processing method, a program, and a measuring system capable of precise fixed point observation.

BACKGROUND ART

In the related art, there exist measuring instruments that measure the state of a user's skin. By using such a measuring instrument to measure the same area of skin, for example, a user is able to perform fixed point observation of chronological changes in his or her skin state.

However, since the user relies on his or her memory of taking measurements to determine the previously measured area and to take a measurement, it is difficult to precisely observe the same area.

Accordingly, there exists a display recognition method configured to cause a user to recognize a previously measured area by presenting a display on a display device that indicates to the user using the measuring instrument, together with the same area of skin that was previously measured (see PTL 1, for example).

CITATION LIST

Patent Literature

[PTL 1]
Japanese Unexamined Patent Application Publication No. 2010-284239

SUMMARY OF INVENTION

Technical Problem

However, according to the display recognition method of the related art, although the user is able to recognize a previously measured area, it is difficult to accurately move the measuring instrument to a position enabling the measurement of that area.

In other words, the user moves the measuring instrument and causes the measuring instrument to measure his or her skin upon determining that the measuring instrument has moved to a position enabling the measurement of the same area as before, but the position determined by the user is not strictly limited to being the position enabling the measurement of the same area as before.

For this reason, it has been difficult to precisely observe the same area of skin, even in the case of using the display recognition method of the related art.

The present disclosure has been devised in light of such circumstances, and is capable of precise fixed point observation.

Solution to Problem

A measuring system for performing a fixed point observation according to a first embodiment of the present disclosure includes at least one image sensor, a measuring instrument including at least one marker, a position computing unit, a determining unit, and an output controller, wherein the imaging unit is configured to acquire an image comprising a user and the marker, and provide the acquired image to the position computing unit, wherein the position computing unit is configured to compute a position of the marker with respect to the user based on the image provided by the imaging unit, and further provide the computed position to the determining unit, wherein the determining unit is configured to determine whether the computed position of the marker matches a retrieved measurement position, and further output the result of the determination to the output controller, and wherein the output controller is configured to provide an indication when the marker position matches the measurement position.

The measuring system may further include a user identifying unit configured to receive an image from the imaging unit, detect one or more features associated with the user, and identify a user based on the detected one or more features. The retrieved measurement position may be a measurement position associated with the identified user.

The marker may be an LED that emits at least one of visible light, ultraviolet light and infrared light.

The marker may also be a light emitter that blinks in a predetermined blinking pattern by turning on and off, and the measuring system further include a pattern detector that detects the blinking pattern of the marker on the basis of whether the marker is on or off in the image.

The measuring instrument may further acquire measurement data in response to the retrieved measurement position matching the computed position of the LED.

The measurement data may comprise skin measurement data.

The measuring instrument may measure the user's skin by taking an image in close proximity, and the measuring system may further include a generator that, on the basis of a plurality of skin images obtained from the measurement unit, generates a full skin image formed by joining the plurality of skin images together.

The measuring system may further include an irradiating unit configured to successively emit light at different wavelengths. The measuring instrument may acquire measurement data for each successive light emission.

The measuring system may further acquire skin measurement data utilizing the measurement instrument.

The measuring instrument may be freely attachable to and detachable from the imaging unit.

The measuring system may further include an orientation identifying unit that identifies the orientation of the measuring instrument.

The measuring instrument may include a sensor that senses the motion of the measuring instrument, and the orientation identifying unit identifies the orientation of the measuring instrument on the basis of the sensing results from the sensor.

The marker may be a graphical figure provided on a case of the measuring instrument and the orientation identifying unit may identify the orientation of the measuring instrument on the basis of the shape of the graphical figure in the image.

A method of performing a fixed point observation according to an embodiment of the present disclosure, may include receiving an image comprising a user and a measuring unit, determining a position of the measuring unit based on the received image; retrieving a stored measurement position associated with the measuring unit, determining if the retrieved measurement position associated with the measuring unit matches the determined position of the measuring unit, and providing an indication that the retrieved measurement position associated with the measuring unit matches the determined position of the measuring unit.

The method of performing a fixed point observation may further include identifying the user based on the received image, wherein retrieving a stored measurement position further comprises retrieving a measurement position associated with the identified user.

The position of the measuring unit may be determined by calculating a position of a marker associated with the measuring unit.

The marker may be a light emitter that blinks in a predetermined blinking pattern by turning on and off, and the method may further include detecting the blinking pattern of the marker on the basis of whether the marker is on or off in the image.

The method of performing a fixed point observation may further include displaying an image comprising an image of the user and an image of the measuring unit to an imaging unit display.

The method of performing a fixed point observation may further acquire measure data from the measurement unit in response to an indication that the retrieved measurement position associated with the measuring unit matches the determined position of the measuring unit.

The image may be acquired at an imaging unit and the position of the measuring unit may be based on a position of an LED associated with the measuring unit.

The method of performing a fixed point observation may further acquire skin measurement data using the measurement unit.

The measuring unit may measure the user's skin by taking an image in close proximity and further generate, on the basis of a plurality of skin images obtained from the measurement unit, a full skin image formed by joining the plurality of skin images together.

The method of performing a fixed point observation may further include identifying a state associated with the measuring unit, where the state of the measuring unit may be at least one of on and off, and displaying the state of the measuring unit and at least one image.

The method of performing a fixed point observation may further include storing the determined position of the measuring unit as a new measurement position, receiving a second image comprising the user and the measuring unit, determining the position of the measuring unit based on the received image, retrieving the new measurement position, determining if the retrieved new measurement position of the measuring unit matches the determined position of the measuring unit, and providing an indication that the retrieved new measurement position of the measuring unit matches the determined position of the measuring unit.

The method of performing a fixed point observation may further include receiving depth information indicating positions in a depth direction, receiving measurement information from the measurement unit, the measurement information comprising skin image data, and generating a three-dimensional image map based on the received depth information and the received measurement information.

The method of performing a fixed point observation may further include receiving measurement information corresponding to different wavelengths of light.

A method of performing a fixed point observation according to at least one embodiment of the present disclosure may comprise determining a position of a measuring instrument based on an image of the measuring instrument, and initiating a measurement by the measuring instrument when the position of the measuring instrument matches a retrieved measurement position.

The measurement by the measuring instrument may be skin measurement data.

The determined position of the measuring instrument may be based on a position of the measuring instrument in an image in relation to a user in the image.

Advantageous Effects of Invention

According to the present disclosure, precise fixed point observation becomes possible.

DESCRIPTION OF EMBODIMENTS

Hereinafter, embodiments for carrying out the present disclosure (hereinafter designated embodiments) will be described. The description will proceed in the following order.

1. First embodiment (example of reporting when LED position matches measurement position)
2. Second embodiment (example of displaying state of measuring instrument according to LED blinking pattern)
3. Third embodiment (example of performing measurement when LED position matches measurement position)
4. Modifications 1. First Embodiment Exemplary Configuration of Measuring System 1

Figure 1:
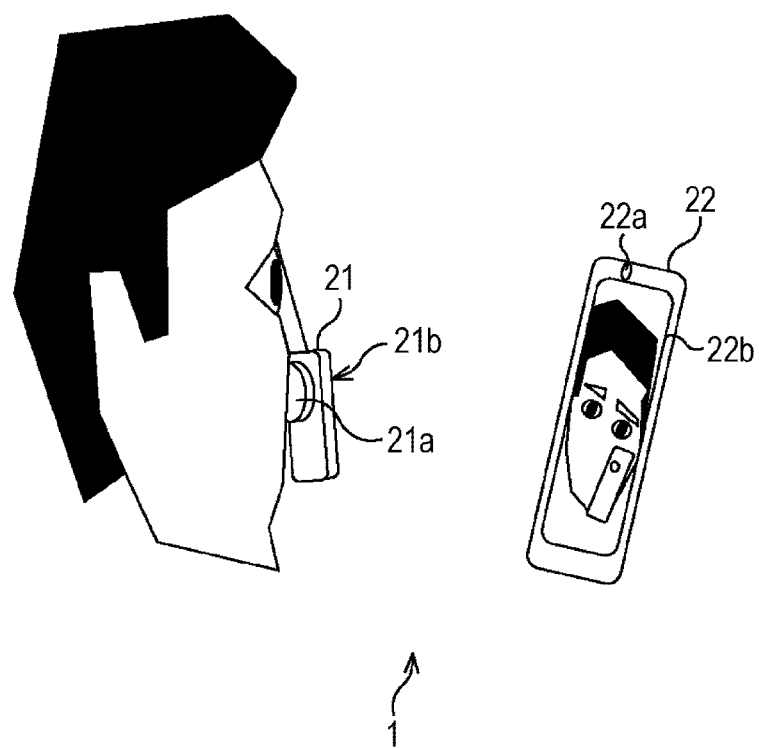
FIG. 1 is a diagram illustrating an exemplary configuration of a measuring system in the present disclosure.

FIG. 1 illustrates an exemplary configuration of a measuring system 1 in the present disclosure.

The measuring system 1 includes a measuring instrument 21 and a smartphone 22, for example, and is capable of performing fixed point observation of skin data regarding a user's skin with the measuring instrument 21.

Note that although the measuring system 1 is described as a system that performs fixed point observation of skin data in the present disclosure, the target of fixed point observation is not limited to skin data, and data regarding features such as the scalp and hair roots, or data expressing the extent (degree) of deterioration in a work of art such as a sculpture, may also be targeted.

The measuring instrument 21 is moved in close proximity to the user's skin (the user's face, for example), and measures skin data regarding the user's skin. Herein, close proximity designates a concept that includes both contact, which represents a distance of zero to the user's skin, and nearness, which represents a short distance to the user's skin.

Also, the data adopted as skin data may be data expressing the state of the user's skin (numerical data indicating factors such as skin elasticity and looseness), or data used to determine the state of the user's skin (a skin image obtained by imaging the skin, for example).

Note that in the first embodiment, the measuring instrument 21 includes a built-in camera 21a that takes a close-up image of the user's skin, and will be described as an instrument that uses the built-in camera 21a to measure skin data in the form of a skin image. However, the skin data measuring method by the measuring instrument 21 is not limited to a measuring method using the camera 21a, and may be any measuring method capable of measuring skin data.

Also, in the measuring instrument 21, a light-emitting diode (LED) 21b is provided on the back of the measuring instrument 21 (the face on the opposite of the face in close proximity to the user's skin). The LED 21b turns on to allow the smartphone 22 to identify the position of the measuring instrument 21.

Note that although the LED 21b is provided on the measuring instrument 21, the marker is not limited to the LED 21b insofar as the marker allows the smartphone 22 to identify the position of the measuring instrument 21, and any such marker may be provided. For example, a graphical figure such as a two-dimensional barcode may be implemented as a marker.

The smartphone 22 includes an imaging unit 22a that takes an image of the user as well as the LED 21b as subjects, and a liquid crystal display (LCD) 22b that displays information such as an image obtained from imaging by the imaging unit 22a.

Note that the LED 21b turns on by emitting light at a wavelength able to be sensed (recognized) by the imaging unit 22a. Besides visible light, the LED 21b may also be configured to emit invisible light such as ultraviolet or infrared light, in order to avoid glare caused by the LED 21b.

This similarly applies to the case where the LED 21b blinks, as discussed later with FIGS. 4 and 5.

As illustrated in FIG. 1, with the measuring instrument 21 in a state of close proximity to the face, the user moves the measuring instrument 21 while referring to an image displayed on the LCD 22b of the smartphone 22.

On the basis of the image obtained from the imaging unit 22a, the smartphone 22 determines whether or not the position of the LED 21b with respect to the user (the LED position) is a measurement position representing the position of the LED when performing a measurement with the measuring instrument 21.

The smartphone 22 then conducts a reporting process that reports in the case of determining that the LED position is the measurement position, for example. At this point, the user is able to perform fixed point observation of the same area on his or her face by operating the measuring instrument 21 and causing the measuring instrument 21 to take a measurement.

In other words, the measuring instrument 21 is able to continually measure a skin image of the same area on the user's face.

Note that the reporting process conducted by the smartphone 22 will be discussed in detail with reference to FIGS. 2 and 3. The smartphone 22 also conducts processes different from the reporting process, and these processes will be described with FIG. 4 and subsequent drawings.

Figure 2:
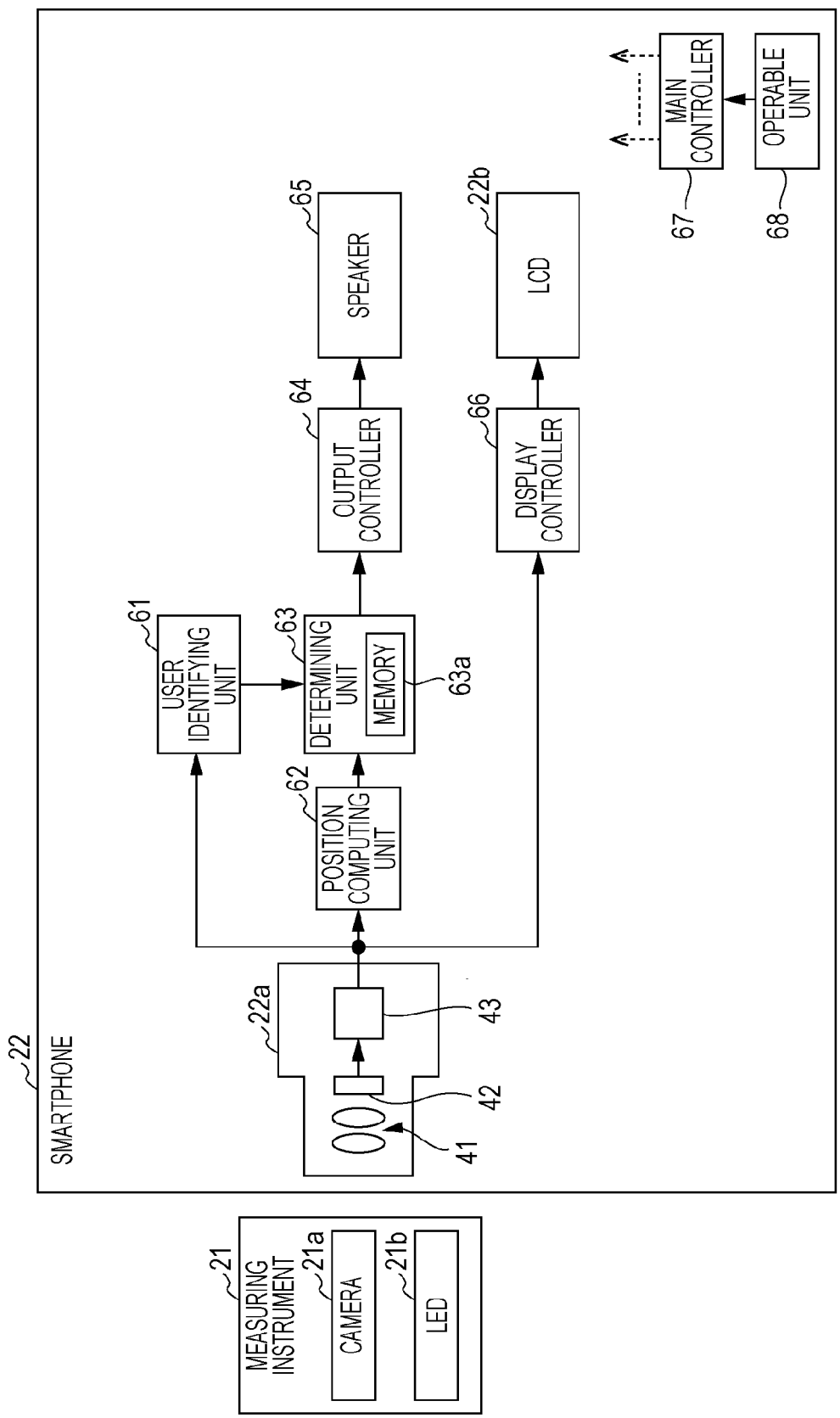
FIG. 2 is a block diagram illustrating a first exemplary configuration of the smartphone in FIG. 1.

Next, FIG. 2 illustrates a first exemplary configuration of the smartphone 22 in FIG. 1.

Besides the imaging unit 22a and the LCD 22b, the smartphone 22 in FIG. 2 includes a user identifying unit 61, a position computing unit 62, a determining unit 63, an output controller 64, a speaker 65, a display controller 66, a main controller 67, and an operable unit 68.

Note that the imaging unit 22a takes an image of the user and the LED 21b of the measuring instrument 21, and supplies the image obtained by such imaging to the user identifying unit 61, the position computing unit 62, and the display controller 66.

The imaging unit 22a includes optics 41, an image sensor 42, and a signal processing integrated circuit (IC) 43.

The optics 41 include components such as a lens that condenses incident light (such as reflected light from the user, for example), and a diaphragm (not illustrated) that adjusts the amount of incident light. The optics 41 focus the incident light onto the light-sensing face of the image sensor 42.

The image sensor 42 photoelectrically converts the light focused by the optics 41, and outputs an image signal obtained as a result to signal processing IC 43. Note that an image sensor such as a charge-coupled device (CCD) or complementary metal-oxide-semiconductor (CMOS) image sensor may be implemented as the image sensor 42, for example.

The signal processing IC 43 subjects the image signal from the image sensor 42 to image processing, and supplies an image expressing the processed image signal to the user identifying unit 61, the position computing unit 62, and the display controller 66.

The user identifying unit 61 identifies the user as an imaged subject on the basis of the image from the imaging unit 22a.

In other words, the user identifying unit 61 detects features such as the user's face from the image from the imaging unit 22a, and identifies the user on the basis of the detection results, for example. The user identifying unit 61 then supplies the identification result to the determining unit 63.

Note that a method that detects skin color portions from the entire image area as the user's face may be implemented as the method of detecting features such as the user's face, for example.

The position computing unit 62 computes the position of the LED 21b with respect to the user (the LED position) on the basis of the image from the imaging unit 22a, and supplies the computed LED position to the determining unit 63.

In other words, the position computing unit 62 detects regions of skin color from the image from the imaging unit 22a as the user's face, and in addition, detects a region of luma equal to or greater than a predetermined threshold as the turned-on LED 21b, for example. Note that the LED 21b is turned on by the measuring instrument 21 in order to compute the LED position.

The position computing unit 62 then computes the LED position on the basis of the detection results for the user's face and the LED 21b, and supplies the computed LED position to the determining unit 63.

The determining unit 63 includes built-in memory 63a. The memory 63a stores measurement positions in association with each of multiple different users. Herein, a measurement position refers to the LED position when measuring the same area with the measuring instrument 21 for fixed point observation. The LED position from a previous measurement by the measuring instrument 21 may be adopted as the measurement position, for example.

Note that the memory 63a may be configured to store multiple positions rather than one position as the measurement position.

In other words, in the case where the measurement region representing the area measured by the measuring instrument 21 is a small region able to be measured with a single measurement, one measurement position measuring that region is stored.

Meanwhile, in the case where the measurement region is a large region involving multiple measurements, as with the measurement region 121 illustrated in FIG. 8 discussed later, multiple measurement positions measuring that region are stored.

Note that in the case where only one user uses the measuring instrument 21, the memory 63a may store only a measurement position for that user. In this case, the user identifying unit 61 may be omitted from the smartphone 22 in FIG. 2.

On the basis of an identification result from the user identifying unit 61, the determining unit 63 retrieves a measurement position associated with the user identified by the user identifying unit 61 from the memory 63a.

The determining unit 63 then determines whether or not the LED position from the position computing unit 62 matches the measurement position retrieved from the memory 63a, and if matching, reports the result to the output controller 64.

In response to receiving a report from the determining unit 63, the output controller 64 controls the speaker 65, causing the speaker 65 to output a tone indicating that the LED position matches the measurement position.

Note that in the first embodiment, in the case where the LED position matches the measurement position, the smartphone 22 in FIG. 2 reports the result to the user by outputting a tone from the speaker 65. However, the reporting method is not limited thereto.

In other words, the smartphone 22 in FIG. 2 may also use at least one of the speaker 65 and the LCD 22b, for example, to report to the user that the LED position matches the measurement position.

In the case of displaying that the LED position matches the measurement position on the LCD 22b, the display controller 66 controls the LCD 22b in response to receiving a report from the determining unit 63, and causes the LCD 22b to display a display indicating that the LED position matches the measurement position.

This case assumes that in the case where the LED position matches the measurement position, the determining unit 63 reports the result to the display controller 66.

The speaker 65 outputs a tone under control by the output controller 64, for example. Note that since the first embodiment is described taking the smartphone 22 as an example, the speaker 65 is configured as part of the smartphone 22. However, the speaker 65 may also be provided externally. Similar reasoning also applies to the LCD 22b.

The display controller 66 supplies an image from the imaging unit 22a to the LCD 22b for display. Thus, an image depicting the user together with the measuring instrument 21 is displayed on the LCD 22b, as illustrated in FIG. 1.

As another example, the display controller 66 may also superimpose a position display representing the measurement position onto an image from the imaging unit 22a, and cause the LCD 22b to display the superimposed image.

In this case, the LED 21b of the measuring instrument 21 and the position display are displayed on the LCD 22b. The user then moves the measuring instrument 21 to align the LED 21b of the measuring instrument 21 with the position display while referring to the display screen on the LCD 22b.

Thus, the user becomes able to more rapidly perform fixed point observation with the measuring instrument 21 compared to the case where a position display is not displayed on the LCD 22b.

As another example, in the case where the measurement target of the measuring instrument 21 is a large region involving multiple measurements as with the measurement region 121 illustrated in FIG. 8 discussed later, for example, the display controller 66 may differentiate the display of measured areas and unmeasured areas in the measurement region 121.

In this case, the user is able to easily ascertain the measured areas and the unmeasured areas by referring to the LCD 22b, thereby preventing missed measurements with the measuring instrument 21.

Otherwise, the display controller 66 may also ignore (discard) an image from the imaging unit 22a and not display an image on the LCD 22b, for example.

The main controller 67 controls the imaging unit 22a, the user identifying unit 61, the position computing unit 62, the determining unit 63, the output controller 64, and the display controller 66 on the basis of an operation signal from the operable unit 68, for example.

The operable unit 68 includes elements such as operable buttons operated by the user, and in response to being operated by the user, supplies the main controller 67 with an operation signal corresponding to the user operation. Note that the operable unit 68 may also be provided on the LCD 22b as a touch panel that senses touch operations from the user.

<Behavior of Smartphone 22 in FIG. 2>

Next, a reporting process conducted by the smartphone 22 in FIG. 2 will be described with reference to the flowchart in FIG. 3.

The reporting process starts when, for example, the user uses the operable unit 68 to perform an activation operation that activates an application that executes the reporting process.

At this point, the operable unit 68 supplies the main controller 67 with an operation signal corresponding to the user's activation operation. The main controller 67 controls the imaging unit 22a, the user identifying unit 61, the position computing unit 62, the determining unit 63, the output controller 64, and the display controller 66 on the basis of the operation signal from the operable unit 68.

Note that the LED 21b is assumed to be turned on when executing the reporting process.

In step S21, the imaging unit 22a, under control by the main controller 67, takes an image of the user and the LED 21b, and supplies the image obtained by such imaging to the user identifying unit 61, the position computing unit 62, and the display controller 66.

In step S22, the user identifying unit 61 identifies the user as an imaged subject on the basis of the image from the imaging unit 22a, and supplies the identification result to the determining unit 63.

In step S23, the position computing unit 62 computes the position of the LED 21b with respect to the user as the LED position on the basis of the image from the imaging unit 22a, and supplies the computed LED position to the determining unit 63.

In step S24, the determining unit 63, on the basis of the identification result from the user identifying unit 61, retrieves a measurement position associated with the user identified by the processing in step S22 from the internal memory 63a.

The determining unit 63 then determines whether or not the LED position from the position computing unit 62 matches the measurement position retrieved from the memory 63a, and if matching, reports the result to the output controller 64, and the process advances to step S25.

In step S25, the output controller 64, in response to receiving a report from the determining unit 63, controls the speaker 65, causing the speaker 65 to output a tone indicating that the LED position matches the measurement position.

Note that in the case where the determining unit 63 determines in step S24 that the LED position from the position computing unit 62 does not match the measurement position retrieved from the memory 63a, the process skips step S25 and advances to step S26.

In step S26, the display controller 66 supplies an image from the imaging unit 22a to the LCD 22b for display. Thus, an image depicting the user together with the measuring instrument 21 is displayed on the LCD 22b, as illustrated in FIG. 1.

In step S27, the imaging unit 22a takes an image of the user and the LED 21b of the measuring instrument 21, and supplies the image obtained by such imaging to the user identifying unit 61, the position computing unit 62, and the display controller 66, similarly to the case of step S21. After that, the process returns to step S23, and similar processing is conducted thereafter.

Note that the reporting process ends when, for example, the user uses the operable unit 68 to perform an operation that ends the application that executes the reporting process.

According to the reporting process as described above, in the case where the LED position matches the measurement position, the output controller 64 controls the speaker 65 to output a tone indicating the result, for example.

Thus, the user is able to easily recognize that the LED position matches the measurement position by the tone from the speaker 65.

Consequently, by pressing a measure button (not illustrated) causing the measuring instrument 21 to take a measurement when the speaker 65 outputs a tone, the user is able to repeatedly cause the measuring instrument 21 to measure skin data from the same area of the user's face.

Thus, the user becomes able to perform fixed point observation of the same area of the user's face using the measuring instrument 21.

Also, since the user may cause the measuring instrument 21 to take a skin measurement only when the speaker 65 outputs a tone, it is possible to reduce power consumption compared to the case of causing the measuring instrument 21 to continually take skin measurements.

Meanwhile, although the LED 21b is configured to be continuously on when executing the reporting process in the first embodiment, the measuring instrument 21 may also be configured to make the LED 21b blink in a blinking pattern that indicates the start of a skin data measurement, for example.

In this case, the smartphone 22 detects the blinking pattern of the LED 21b on the basis of the LED 21b being on or off in images obtained from the imaging unit 22a, and conducts a state displaying process that displays on the LCD 22b the state of the measuring instrument 21 as indicated by the detected blinking pattern. The state displaying process will be described in detail with reference to FIGS. 4 and 5 as the second embodiment.

Herein, states such as the measurement progress state and the imaging state of the camera 21a built into the measuring instrument 21 may be adopted as states of the measuring instrument 21, for example.

Note that the measurement progress state may be considered to be a state indicating that measurement is starting, a state indicating that skin data is being measured, or a state indicating that measurement is ending, for example.

Meanwhile, in the case where the camera 21a operates in multiple operating modes, the imaging state of the camera 21a may be considered to be a state indicating an operating mode that takes an image of skin illuminated with visible light, or a state indicating an operating mode that takes an image of skin illuminated with infrared light, for example.

2. Second Embodiment

Exemplary Configuration of Smartphone 22 According to Second Embodiment

Figure 4:
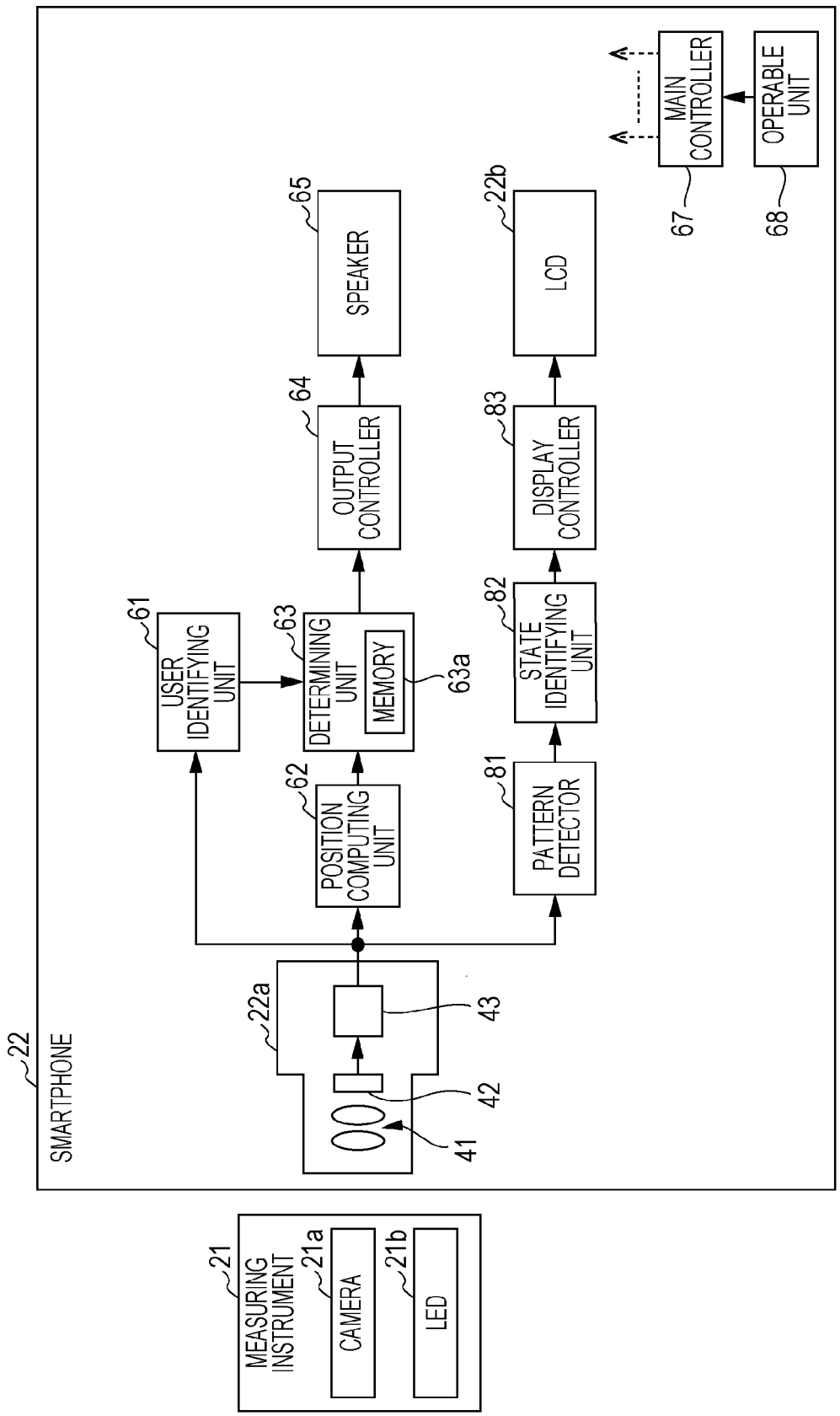
FIG. 4 is a block diagram illustrating a second exemplary configuration of the smartphone in FIG. 1.

Next, FIG. 4 illustrates an exemplary configuration of a smartphone 22 able to display an image with a superimposed state display.

Note that in the smartphone 22 in FIG. 4, portions configured similarly as in the case of FIG. 2 are denoted with the same reference signs, and the description of such portions may be reduced or omitted hereinafter.

In other words, the smartphone 22 in FIG. 4 is configured similarly as in the case of FIG. 2, except that a pattern detector 81, a state identifying unit 82, and a display controller 83 are provided instead of the display controller 66 in FIG. 2.

The pattern detector 81 is supplied with images from the imaging unit 22a. The pattern detector 81 detects whether the LED 21b is on or off, on the basis of the images supplied from the imaging unit 22a.

In other words, the pattern detector 81 detects that the LED 21b is on in the case where luma equal to or greater than a predetermined threshold exists among the respective luma values in an image from the imaging unit 22a, and detects that the LED 21*b* is off in the case where luma equal to or greater than the threshold does not exist.

The pattern detector 81 then supplies the state identifying unit 82 with multiple detection results obtained from the respective images supplied by the imaging unit 22*a* as the blinking pattern of the LED 21*b*, together with the images.

The state identifying unit 82 identifies the state of the measuring instrument 21 on the basis of the blinking pattern from the pattern detector 81, and supplies the display controller 83 with the identification result, together with the images from the pattern detector 81.

In other words, the state identifying unit 82 determines whether or not the blinking pattern from the pattern detector 81 matches a state pattern representing the state of the measuring instrument 21, for example.

Then, in the case of determining that the blinking pattern does not match a state pattern, the state identifying unit 82 supplies the display controller 83 with only the images from the pattern detector 81.

Meanwhile, in the case of determining that the blinking pattern does match a state pattern, the state identifying unit 82 identifies the state indicated by that state pattern as the state of the measuring instrument 21, and supplies the display controller 83 with the identification result, together with the images from the pattern detector 81.

Note that the state identifying unit 82 stores multiple different state patterns in advance in internal memory not illustrated.

The display controller 83 supplies an image from the state identifying unit 82 to the LCD 22*b* for display, similarly to the display controller 66 in FIG. 2.

Also, in the case where the state identifying unit 82 supplies an identification result indicating the state of the measuring instrument 21, the display controller 83 superimposes a state display indicating the state of the measuring instrument 21 onto an image from the state identifying unit 82 on the basis of the identification result.

The display controller 83 then supplies the image with the superimposed state display to the LCD 22*b* for display.

<Behavior of Smartphone 22 in FIG. 4>

Next, a state displaying process conducted by the smartphone 22 in FIG. 4 will be described with reference to the flowchart in FIG. 5.

Figure 3:
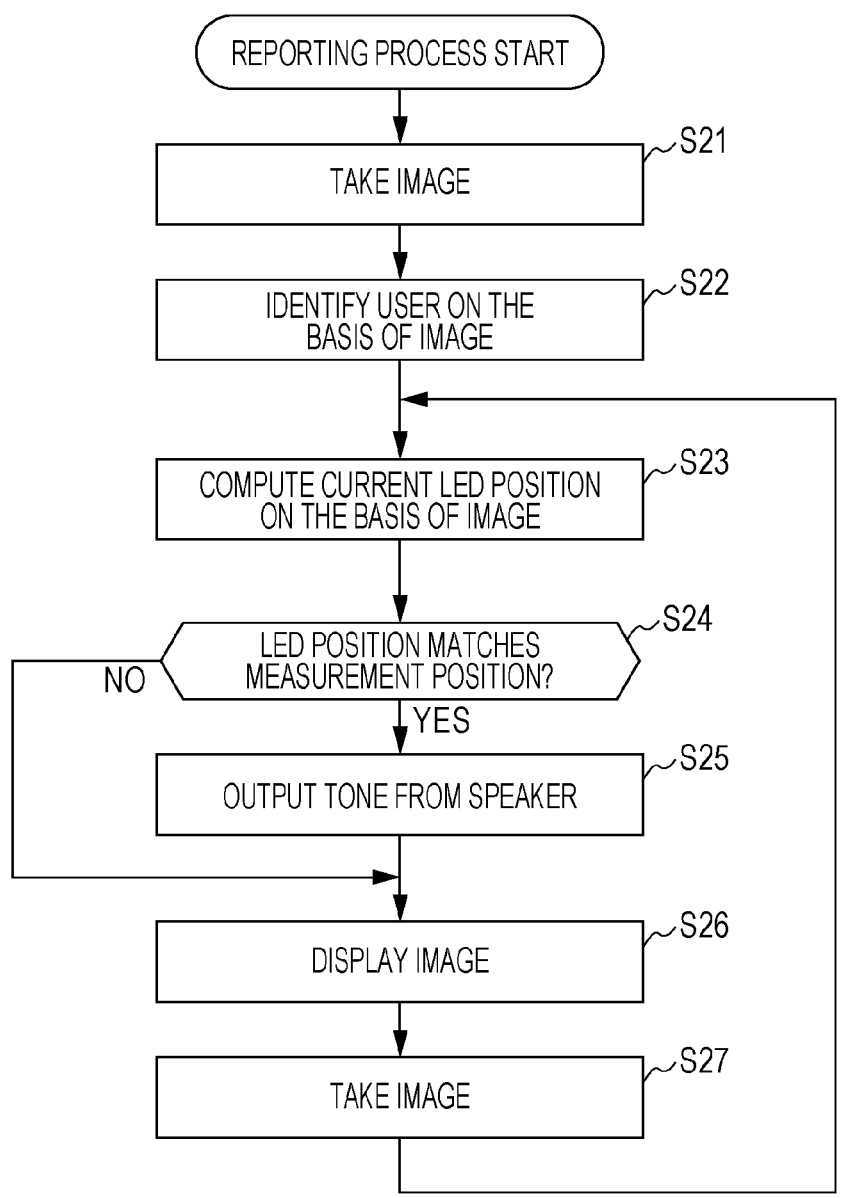
FIG. 3 is a flowchart for illustrating a reporting process conducted by the smartphone in FIG. 2.

Note that the smartphone 22 in FIG. 4 conducts a process similar to the reporting process conducted by the smartphone 22 in FIG. 2, except for conducting the state displaying process instead of the processing in step S26 of FIG. 3. For this reason, the flowchart in FIG. 5 only illustrates the state displaying process.

In step S41, the pattern detector 81 detects whether the LED 21*b* is on or off, on the basis of images supplied from the imaging unit 22*a*.

In other words, the pattern detector 81 detects that the LED 21*b* is on in the case where luma equal to or greater than a predetermined threshold exists among the respective luma values in an image from the imaging unit 22*a*, and detects that the LED 21*b* is off in the case where luma equal to or greater than the threshold does not exist.

The pattern detector 81 then supplies the state identifying unit 82 with multiple detection results obtained from respective images supplied by the imaging unit 22*a* as the blinking pattern of the LED 21*b*, together with the images.

In step S42, the state identifying unit 82 determines whether or not the blinking pattern from the pattern detector 81 matches a state pattern representing the state of the measuring instrument 21.

Then, in the case of determining that the blinking pattern does not match a state pattern, the state identifying unit 82 supplies the display controller 83 with only the images from the pattern detector 81, and the process advances to step S43.

In step S43, the display controller 83 supplies an image from the state identifying unit 82 to the LCD 22*b* for display as-is, and the state displaying process ends.

Meanwhile, in the case where the state identifying unit 82 determines in step S42 that the blinking pattern does match a state pattern, the process advances to step S44, and the state identifying unit 82 identifies the state indicated by that state pattern as the state of the measuring instrument 21.

The state identifying unit 82 then supplies the display controller 83 with the identification result together with the images from the pattern detector 81, and the process proceeds to step S45.

In step S45, the display controller 83 superimposes a state display indicating the state of the measuring instrument 21 onto an image from the state identifying unit 82, on the basis of the identification result indicating the state of the measuring instrument 21 from the same state identifying unit 82.

The display controller 83 then supplies the image with the superimposed state display to the LCD 22*b* for display, and the state displaying process ends.

According to the state displaying process as described above, the display controller 83 causes the LCD 22*b* to display the state of the measuring instrument 21 on the basis of a blinking pattern by the LED 21*b* of the measuring instrument 21.

Thus, the user becomes able to easily ascertain the state of the measuring instrument 21 (such as a state where the measuring instrument 21 is taking a measurement, for example) by referring to the LCD 22*b* of the smartphone 22 in FIG. 4.

Note that the smartphone 22 may be configured such that, in the case of determining that the LED position is the measurement position, the smartphone 22 controls the measuring instrument 21 and conducts a measurement controlling process that causes the measuring instrument 21 to take a skin measurement. The measurement controlling process will be described in detail with reference to FIGS. 6 and 7 as the third embodiment.

3. Third Embodiment

Exemplary Configuration of Smartphone 22 According to Third Embodiment

Figure 6:
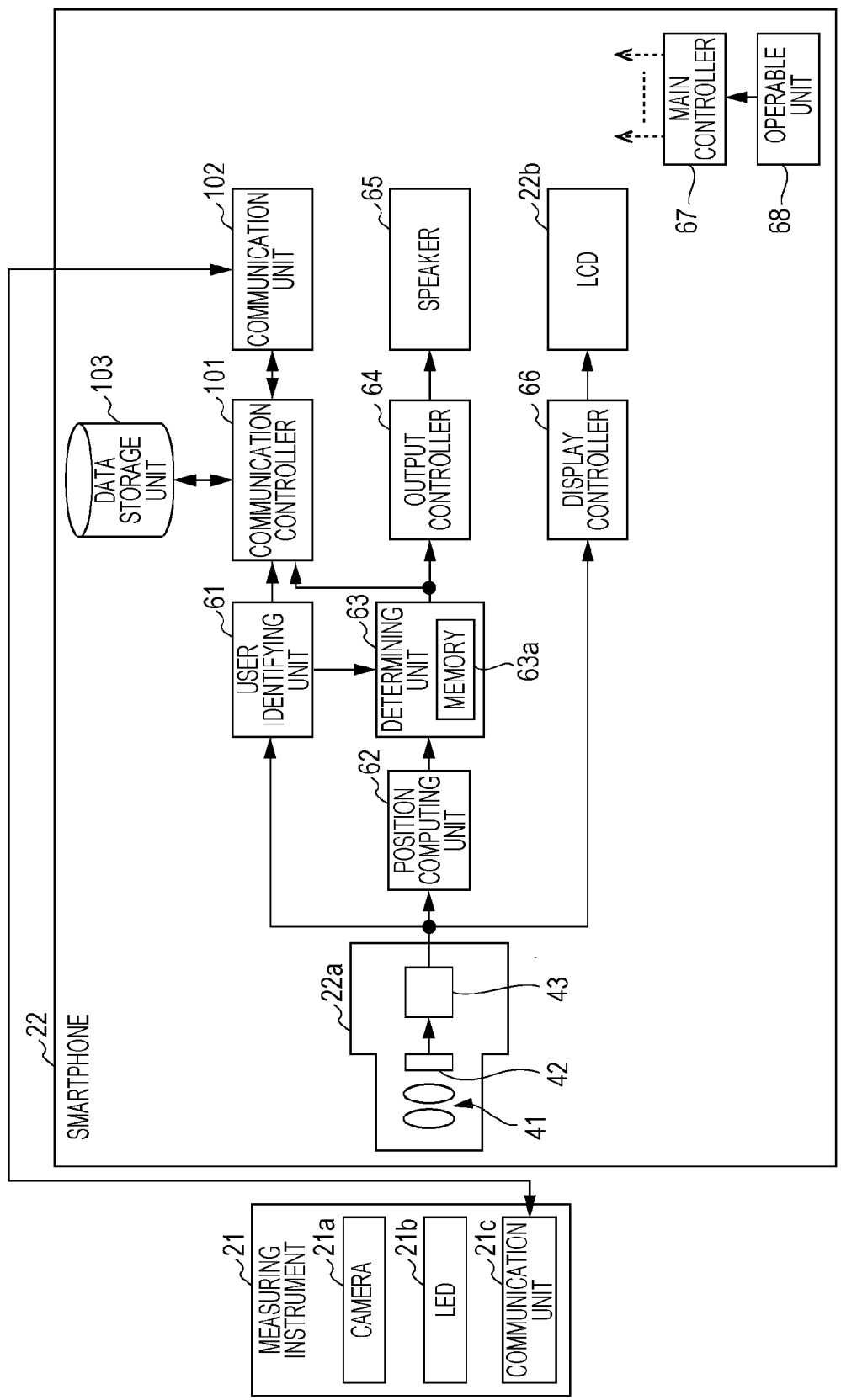
FIG. 6 is a block diagram illustrating a third exemplary configuration of the smartphone in FIG. 1.

Next, FIG. 6 illustrates an exemplary configuration of a smartphone 22 that controls the measuring instrument 21 to measure skin data.

Note that in the smartphone 22 in FIG. 6, portions configured similarly as in the case of FIG. 2 are denoted with the same reference signs, and the description of such portions may be reduced or omitted hereinafter.

In other words, the smartphone 22 in FIG. 6 is configured similarly as in the case of FIG. 2, except that a communication controller 101, a communication unit 102, and a data storage unit 103 are additionally provided.

Also, in the third embodiment, the display controller 66 in FIG. 6 may be configured to function as the pattern detector 81, the state identifying unit 82, and the display controller 83 in FIG. 4.

In other words, in the third embodiment, with the configuration illustrated in FIG. 6, the smartphone 22 in FIG. 6 is able to conduct at least one of a reporting process similar to the smartphone 22 in FIG. 2 or the measurement controlling process in the case where the LED position matches the measurement position.

Furthermore, if the display controller 66 in FIG. 6 is configured to function as the pattern detector 81 to the display controller 83 in FIG. 4, the smartphone 22 in FIG. 6 is able to conduct at least one of a reporting process similar to the smartphone 22 in FIG. 2 or the measurement controlling process in the case where the LED position matches the measurement position.

Also, in FIG. 6, besides the camera 21a and the LED 21b, the measuring instrument 21 is provided with a communication unit 21c that wirelessly communicates with the smartphone 22.

Note that although the third embodiment describes the measuring instrument 21 and the smartphone 22 communicating wirelessly, the measuring instrument 21 and the smartphone 22 may also be connected by a cable and communicate via the cable.

The communication controller 101 controls the communication unit 102 and communicates data with the measuring instrument 21 by wireless communication such as Wi-Fi (trademark) or Bluetooth (registered trademark).

In other words, the communication controller 101 controls the communication unit 102 to transmit a control signal to the measuring instrument 21, and receive skin data (a skin image, for example) from the measuring instrument 21, for example.

Specifically, in response to a report from the user identifying unit 61 or a report from the determining unit 63, the communication controller 101 may supply a control signal for controlling the measuring instrument 21 to the communication unit 102 for transmission, for example.

Note that the user identifying unit 61 is assumed to report to the communication controller 101 in the case of identifying a user as an imaged subject, while the determining unit 63 is assumed to report to the communication controller 101 in the case of determining that the LED position matches a measurement position.

Herein, signals such as an ON instruction signal instructing the LED 21b to turn on, an OFF instruction signal instructing the LED 21b to turn off, and a measure instruction signal instructing the measuring instrument 21 to take a measurement may be adopted as a control signal, for example.

As another example, the communication controller 101 may receive a skin image, for example, as skin data from the measuring instrument 21 via the communication unit 102, and cause the data storage unit 103 to store the skin image in association with an LED position from the determining unit 63.

Note that the determining unit 63 is assumed to supply the communication controller 101 with an LED position from the position computing unit 62.

Also, a skin image stored in the data storage unit 103 may be analyzed by analysis software or the like that determines the state of a user's skin, for example. Such analysis software or the like is executed by the main controller 67 in response to a user operation performed using the operable unit 68, for example. Analysis results obtained by the analysis software or the like may be displayed on the LCD 22b, for example.

The communication unit 102, under control by the communication controller 101, transmits information such as a control signal from the communication controller 101 to the measuring instrument 21 by wireless communication, and in addition, receives information such as a skin image from the measuring instrument 21, which is supplied to the communication controller 101.

The data storage unit 103 stores (retains) skin images from the communication controller 101 which are associated with LED positions.

<Behavior of Smartphone 22 in FIG. 6 According to Third Embodiment>

Next, a measurement controlling process conducted by the smartphone 22 in FIG. 6 will be described with reference to the flowchart in FIG. 7.

Note that besides conducting a reporting process similar to that of the smartphone 22 in FIG. 2, the smartphone 22 in FIG. 6 conducts a measurement controlling process as a process different from that of the smartphone 22 in FIG. 2.

In step S61, the communication controller 101 waits for a report identifying a user from the user identifying unit 61, and the process then proceeds to step S62.

In step S62, the communication controller 101 controls the measuring instrument 21 via the communication unit 102, and turns on the LED 21b of the measuring instrument 21.

In other words, the communication controller 101 supplies the communication unit 102 with an ON instruction signal instructing the LED 21b of the measuring instrument 21 to turn on, for example. The communication controller 101 then controls the communication unit 102 to transmit the ON instruction signal from the communication unit 102 to the measuring instrument 21.

Thus, the communication unit 21c in the measuring instrument 21 receives an ON instruction signal from the communication unit 102. A controller (not illustrated) in the measuring instrument 21 then controls the LED 21b to turn on the LED 21b on the basis of the ON instruction signal received by the communication unit 21c.

In step S63, the communication controller 101 waits for a report from the determining unit 63 indicating that the LED position matches a measurement position, and the process then proceeds to step S64.

In step S64, the communication controller 101 controls the measuring instrument 21 via the communication unit 102 to measure a skin image, for example.

In other words, the communication controller 101 supplies the communication unit 102 with a measure instruction signal instructing the measuring instrument 21 to take a measurement, for example. The communication controller 101 then controls the communication unit 102 to transmit the measure instruction signal from the communication unit 102 to the measuring instrument 21.

Thus, the communication unit 21c in the measuring instrument 21 receives a measure instruction signal from the communication unit 102. Then, on the basis of the measure instruction signal received by the communication unit 21c, a controller (not illustrated) in the measuring instrument 21 controls the camera 21a to take an image of the user's skin and transmit the skin image obtained by such imaging to the communication unit 102 via the communication unit 21c.

In step S65, the communication unit 102 receives a skin image from the communication unit 21c of the measuring instrument 21, which is supplied to the communication controller 101.

In step S66, the communication controller 101 stores the skin image from the communication unit 102 in the data storage unit 103, for example, in association with the LED position from the determining unit 63. Note that the determining unit 63 supplies the communication controller 101 with the LED position output from the position computing unit 62.

At this point, the skin image stored in the data storage unit 103 may be analyzed by analysis software or the like that determines the state of the user's skin, for example. The analysis results may then be displayed on the LCD 22*b*, for example.

In step S67, the communication controller 101 controls the measuring instrument 21 via the communication unit 102, and turns off the LED 21*b* of the measuring instrument 21.

In other words, the communication controller 101 supplies the communication unit 102 with an OFF instruction signal instructing the LED 21*b* of the measuring instrument 21 to turn off, for example. The communication controller 101 then controls the communication unit 102 to transmit the OFF instruction signal from the communication unit 102 to the measuring instrument 21.

Thus, the communication unit 21*c* in the measuring instrument 21 receives an OFF instruction signal from the communication unit 102. A controller (not illustrated) in the measuring instrument 21 then controls the LED 21*b* to turn off the LED 21*b* on the basis of the OFF instruction signal received by the communication unit 21*c*. With that, the measurement controlling process ends.

According to the measurement controlling process as described above, in the case where the LED position matches the measurement position, the communication controller 101 controls the measuring instrument 21 via the communication unit 102, causing the measuring instrument 21 to measure a skin image.

Thus, the user is saved the trouble of pressing a measure button (not illustrated) causing the measuring instrument 21 to take a measurement, and is able to repeatedly cause the measuring instrument 21 to measure skin data in the form of a skin image, for example, from the same area of the user's face.

The measuring instrument 21 measures skin data at an LED position that matches a measurement position. However, the measuring instrument 21 may also measure skin data at each of multiple different measurement positions while moving in close proximity to the user's skin, for example.

In other words, it is possible to measure skin data in the form of multiple skin images by having the built-in camera 21*a* in the measuring instrument 21 take an image at each of multiple different measurement positions.

Figure 8:
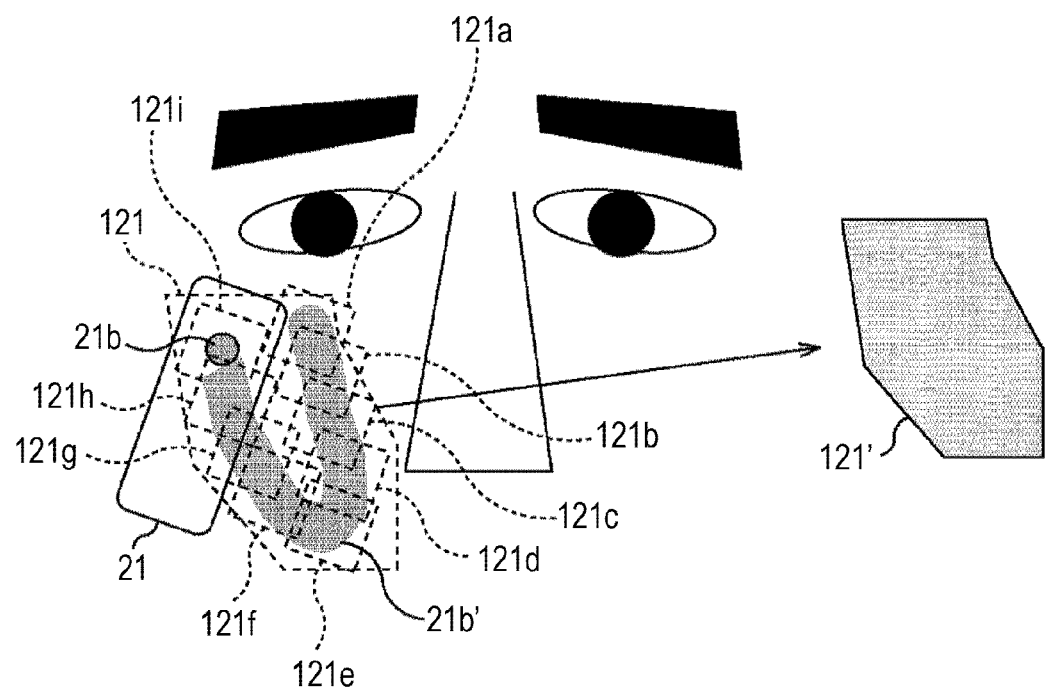
FIG. 8 is a diagram illustrating an example of how a measuring instrument measures multiple skin images.

Next, FIG. 8 illustrates an example of how the measuring instrument 21 measures a skin image at each of multiple different measurement positions while moving in close proximity to the user's skin.

Note that in FIG. 8, the measurement region 121 represents a region measured by the measuring instrument 21, while the skin images 121*a* to 121*i* represent examples of skin images obtained by taking measurements in the measurement region 121.

Also, in FIG. 8, the track 21*b*' represents the track of the LED 21*b* moving within the measurement region 121 while the measuring instrument 21 takes measurements.

Furthermore, in FIG. 8, the full skin image 121' represents an image obtained when imaging the measurement region 121. The full skin image 121' is generated by joining the respective skin images 121*a* to 121*i* illustrated in FIG. 8, for example.

The user moves the measuring instrument 21 such that the LED 21*b* traces the track 21*b*'. In this case, the measuring instrument 21, under control by the smartphone 22 in FIG. 6, measures the skin images 121*a* to 121*i* at respective measurement positions along the track 21*b*', for example. The output controller 64 in the smartphone 22 in FIG. 6 may also control the speaker 65 to output a tone at each measurement position along the track 21*b*'.

Note FIG. 8 assumes that the user moves the measuring instrument 21 such that the LED 21*b* traces the track 21*b*'. However, the track 21*b*' is not limited thereto, and may be a track different from a track during a previous measurement, insofar as the track enables the measuring instrument 21 to measure the skin images 121*a* to 121*i*. In other words, features such as the start position and end position of the track 21*b*' may differ from a track during a previous measurement.

The measuring instrument 21 transmits the skin images 121*a* to 121*i* obtained by measurement to the smartphone 22 in FIG. 6.

The smartphone 22 in FIG. 6 receives the skin images 121*a* to 121*i* from the measuring instrument 21, and generates a full skin image 121' like that illustrated in FIG. 8 on the basis of the received skin images 121*a* to 121*i*.

<Behavior of Smartphone 22 in FIG. 6 when Generating Full Skin Image>

Next, an image compositing process in which the smartphone 22 in FIG. 6 composites the skin images 121*a* to 121*i* to generate the full skin image 121' will be described with reference to the flowchart in FIG. 9.

Figure 7:
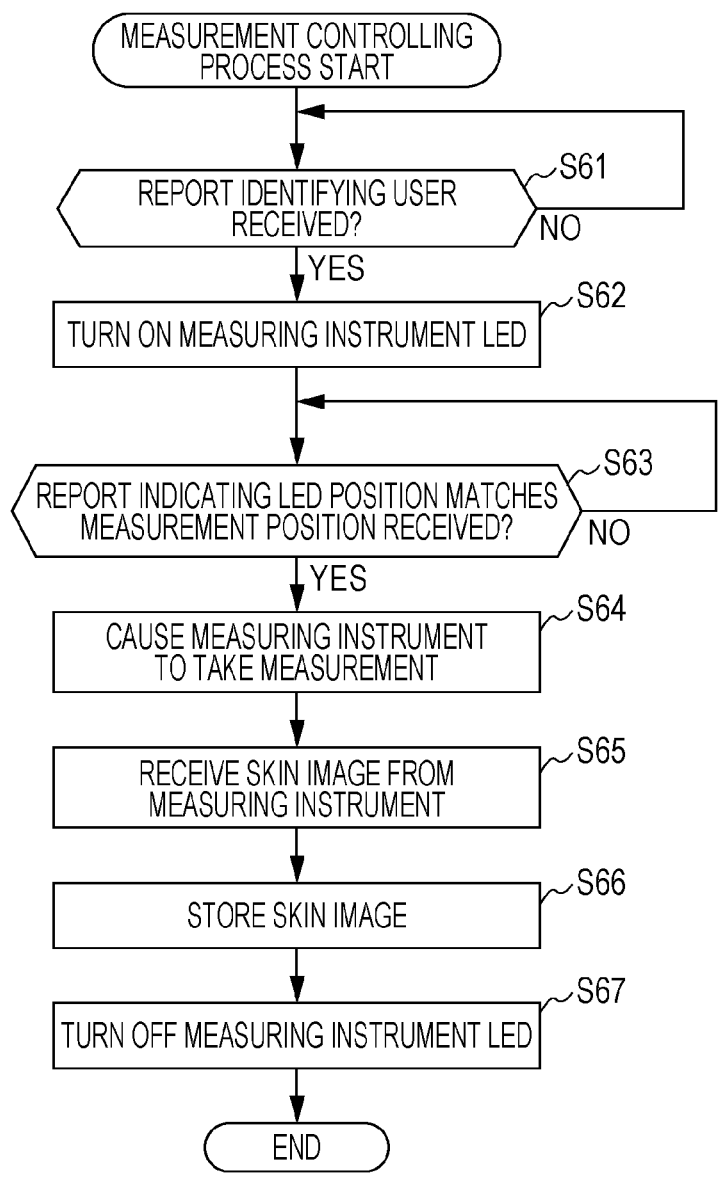
FIG. 7 is a flowchart for illustrating a measurement controlling process conducted by the smartphone in FIG. 6.

In step S81 to step S86, processing similar to that in step S61 to step S66 of FIG. 7 is conducted.

In step S87, the communication controller 101 determines, on the basis of LED positions associated with skin images already stored in the data storage unit 103, whether or not all skin images to be obtained at the respective measurement positions along the track 21*b*' have been measured, for example.

In step S87, in the case where the communication controller 101 determines, on the basis of LED positions associated with skin images already stored in the data storage unit 103, that not all skin images to be obtained at the respective measurement positions along the track 21*b*' have yet been measured, the process returns to step S83.

In step S83, the communication controller 101 determines whether or not the determining unit 63 has reported that the LED position matches a measurement position whose skin image has not yet been measured from among the respective measurement positions along the track 21*b*'.

The communication controller 101 repeats the processing in step S83 until determining that the determining unit 63 has reported, and in the case where the determining unit 63 has reported, the process advances to step S84, and similar processing is conducted thereafter.

Meanwhile, in step S87, in the case where the communication controller 101 determines, on the basis of LED positions associated with skin images already stored in the data storage unit 103, that all skin images to be obtained at the respective measurement positions along the track 21*b*' have been measured, the process advances to step S88.

In step S88, the communication controller 101 retrieves from the data storage unit 103 the skin images 121*a* to 121*i* that were stored in the data storage unit 103 by repeating the processing from step S83 to step S87.

The communication controller 101 then generates a full skin image 121' corresponding to the measurement region 121 on the basis of the retrieved skin images 121*a* to 121*i*, and supplies the generated full skin image 121' to the data storage unit 103 for storage.

In step S89, processing similar to that in step S67 of FIG. 7 is conducted, and the image compositing process ends.

According to the image compositing process as described above, the communication controller 101 generates a full skin image 121' corresponding to the measurement region 121 on the basis of skin images 121a to 121i obtained at respective measurement positions along a track 21b'.

Thus, according to the image compositing process, the smartphone 22 in FIG. 6 becomes able to also acquire a full skin image 121' corresponding to the measurement region 121 that is unfeasible to acquire with a single measurement.

As another example, if the smartphone 22 in FIG. 6 is provided with a distance measuring unit that measures the distance to a measurement position on the basis of an image from the imaging unit 22a, the respective positions of the skin images 121a to 121i in the depth direction (depth information) may also be obtained.

In this case, the smartphone 22 in FIG. 6 is able to generate a full skin image 121' as a three-dimensional image with depth information on the basis of the skin images 121a to 121i and the depth information.

In other words, the smartphone 22 in FIG. 6 is able to compute a three-dimensional position for each of the skin images 121a to 121i from the measurement positions expressed as two-dimensional positions, and the depth information indicating positions in the depth direction, for example.

Thus, by mapping corresponding skin images to the computed three-dimensional position for each of the skin images 121a to 121i, the smartphone 22 in FIG. 6 is able to generate a stereoscopic full skin image 121', which may be displayed on the LCD 22b, for example.

Note that the distance measuring unit is able to measure distance according to the brightness (luma) and size of the LED 21b in an image output from the imaging unit 22a, for example. This utilizes the effect of the LED 21b of the measuring instrument 21 appearing brighter and larger in an image the closer the LED 21b is to the smartphone 22 in FIG. 6.

A depth map generator that generates a depth map respectively indicating the distance to the subject displayed in each pixel of an image may also be adopted as the distance measuring unit, for example.

The depth map generator generates a depth map according to a stereo camera method that uses multiple cameras provided with parallax, or a light-section method that uses a camera and laser slit light, for example.

As another example, the depth map generator may also generate a depth map by using a time-of-flight camera, or a laser rangefinder that measures distance according to a principle similar to a time-of-flight camera.

Herein, a time-of-flight camera refers to a camera which includes a light source that radiates light, and which measures distance on the basis of the time of flight until light from the light source is reflected back and sensed, and the speed of light.

4. Modifications

Modification of Measuring Instrument 21

The measuring instrument 21 takes a skin image as a measurement of skin data by using a built-in camera 21a.

However, the measuring instrument 21 may also be provided with an irradiating unit that emits light at different wavelengths, with the irradiating unit successively irradiating the skin with light at different wavelengths. The camera 21a may then take an image of the skin each time the skin is irradiated with light at a different wavelength.

In this case, by using the camera 21a, the measuring instrument 21 measures images such as a skin image depicting the epidermis of the skin, a skin image depicting the dermis of the skin, and a skin image depicting blood vessels in the skin as different skin images for each wavelength.

This is because the reflectivity of light differs by wavelength in features constituting the skin such as the epidermis, the dermis, and blood vessels. In other words, if for example the irradiating unit radiates light at a wavelength for which the epidermis of the skin has high reflectivity but features such as the dermis of the skin and blood vessels have low reflectivity, the measuring instrument 21 is able to measure a skin image depicting the epidermis of the skin (only) by imaging with the camera 21a.

Thus, the measuring instrument 21 becomes able to measure multiple skin images for determining various states of the skin.

Note that in the case of providing the measuring instrument 21 with an irradiating unit, the skin image measuring method may conceivably be a first measuring method that successively drives the irradiating unit and the camera 21a, or a second measuring method that drives the irradiating unit and the 21a in parallel, for example.

In other words, with the first measuring method, the irradiating unit radiates light at a first wavelength, and the camera 21a images the skin being irradiated with light at the first wavelength, for example.

Next, after stopping the radiation of light at the first wavelength, the irradiating unit radiates light at a second wavelength different from the first wavelength, and the camera 21a images the skin being irradiated with light at the second wavelength.

Thus, the camera 21a is able to obtain a skin image of skin being irradiated with light at a first wavelength, and a skin image of skin being irradiated with light at a second wavelength.

Note that in the case where the measuring instrument 21 measures the measurement region 121, the irradiating unit continues to radiate light at the first wavelength until the camera 21a finishes imaging the skin images 121a to 121i within the measurement region 121.

Also, after the camera 21a finishes imaging the skin images 121a to 121i, the irradiating unit stops radiating light at the first wavelength, and starts radiating light at the second wavelength. The irradiating unit then continues to radiate light at the second wavelength until the camera 21a finishes imaging the skin images 121a to 121i within the measurement region 121.

Thus, the camera 21a is able to obtain skin images 121a to 121i of skin being irradiated with light at the first wavelength, and skin images 121a to 121i of skin being irradiated with light at the second wavelength.

As another example, with the second measuring method, the irradiating unit successively irradiates skin with light at different wavelengths. Meanwhile, the camera 21a takes images in parallel with the radiation by the irradiating unit.

Thus, the camera 21a is able to acquire respective skin images at different wavelengths.

Note that in the case where the measuring instrument 21 measures the measurement region 121, the user is expected to move the measuring instrument 21 at a speed enabling skin images 121a to 121i to be obtained at different wavelengths.

For this reason, in the case where the user is moving the measuring instrument 21 too quickly, it is desirable for the smartphone 22 to report this result to the user, and prompt the user to adjust the speed of the measuring instrument 21, for example. Note that the speaker 65 and the LCD 22b may be used to report to the user.

Also, the smartphone 22 computes the speed of the measuring instrument 21 on the basis of at least one of information regarding the change in the LED position or the motion of the measuring instrument 21.

Herein, information such as the acceleration and angular velocity of the measuring instrument 21 may be adopted as motion information. Note that in the case where the smartphone 22 identifies the speed of the measuring instrument 21 on the basis of information such as the acceleration and angular velocity of the measuring instrument 21, the measuring instrument 21 is provided with various sensors (such as an acceleration sensor and an angular velocity sensor (gyro sensor), for example) that sense information such as the acceleration and angular velocity of the measuring instrument 21.

The measuring instrument 21 then transmits the sensing results obtained from the various sensors to the smartphone 22 as appropriate. The smartphone 22 identifies the speed of the measuring instrument 21 on the basis of the sensing results from the measuring instrument 21, and in the case where the identified speed is equal to or greater than a given speed, reports to the user by displaying a message or the like on the LCD 22b indicating that the movement of the measuring instrument 21 is too fast.

The smartphone 22 is also able to identify the orientation (imaging direction) of the measuring instrument 21 (camera 21a) on the basis of the sensing results from the measuring instrument 21.

For this reason, the smartphone 22 is able to determine whether or not the camera 21a is oriented in accordance with the current LED position (for example, oriented such that the optical axis of the camera 21a is perpendicular to the skin surface).

In the case of determining that the camera 21a is not oriented in accordance with the LED position, the smartphone 22 is able to report to the user by displaying a message on the LCD 22b instructing the user to correct the orientation of the camera 21a to an orientation in accordance with the LED position, for example.

Thus, the user is able to correct the orientation of the camera 21a to an orientation in accordance with the LED position while referring to the LCD 22b of the smartphone 22, thereby making it possible to prevent situations where taking a skin image fails.

Note that although the smartphone 22 is configured to identify the orientation of the camera 21a on the basis of sensing results from the measuring instrument 21 as discussed above, the smartphone 22 may also be configured to identify the orientation of the camera 21a on the basis of an image output from the imaging unit 22a.

This case assumes that a graphical figure such as a two-dimensional barcode is provided on the case of the measuring instrument 21 instead of the LED 21b. The smartphone 22 then identifies the orientation of the camera 21a on the basis of the shape of the graphical figure (such as the deformation of the graphical figure, for example) in an image output from the imaging unit 22a.

Note that the marker provided on the measuring instrument 21 is not limited to being a graphical figure such as a two-dimensional barcode, and any marker for the purpose of identifying the orientation of the camera 21a may be adopted. In other words, LEDs may also be respectively provided on the top, bottom, left, and right sides of the measuring instrument 21 instead of a graphical figure such as a two-dimensional barcode, for example.

The smartphone 22 may also be configured to identify the orientation of the camera 21a on the basis of both sensing results from the measuring instrument 21 and the shape of a graphical figure in an image output from the imaging unit 22a. In this case, the smartphone 22 is able to more precisely identify the orientation of the camera 21a.

Next, other examples of the measuring instrument 21 will be described with reference to FIGS. 10 to 14.

Figure 10:
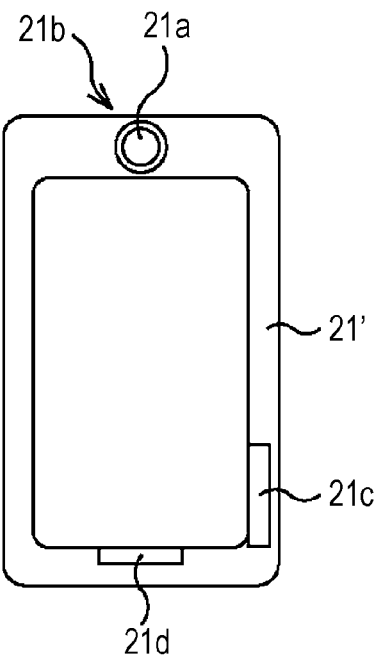
FIG. 10 is a diagram illustrating an example of a jacket-style measuring instrument.

FIG. 10 illustrates an example of a jacket-style measuring instrument 21' which is freely attachable to and detachable from the smartphone 22.

As illustrated in FIG. 10, the measuring instrument 21' has a shape that is attachable to the smartphone 22 so as to cover sides of the smartphone 22, for example. Note that the shape of the measuring instrument 21' is not limited to the shape illustrated in FIG. 10, and may be any shape that is freely attachable to and detachable from the smartphone 22.

The measuring instrument 21' is also provided with a camera 21a, an LED 21b, a communication unit 21c, and a charging connector 21d. Note that the camera 21a to the communication unit 21c are configured similarly to the camera 21a to the communication unit 21c in FIG. 6, and thus are denoted with the same reference signs, and the description thereof is reduced or omitted.

The charging connector 21d is a connector provided to charge a battery (not illustrated) built into the measuring instrument 21'.

The measuring instrument 21' measures a user's skin data similarly to the measuring instrument 21 illustrated in FIG. 1 when detached from the smartphone 22 as illustrated in FIG. 10, for example.

Figure 5:
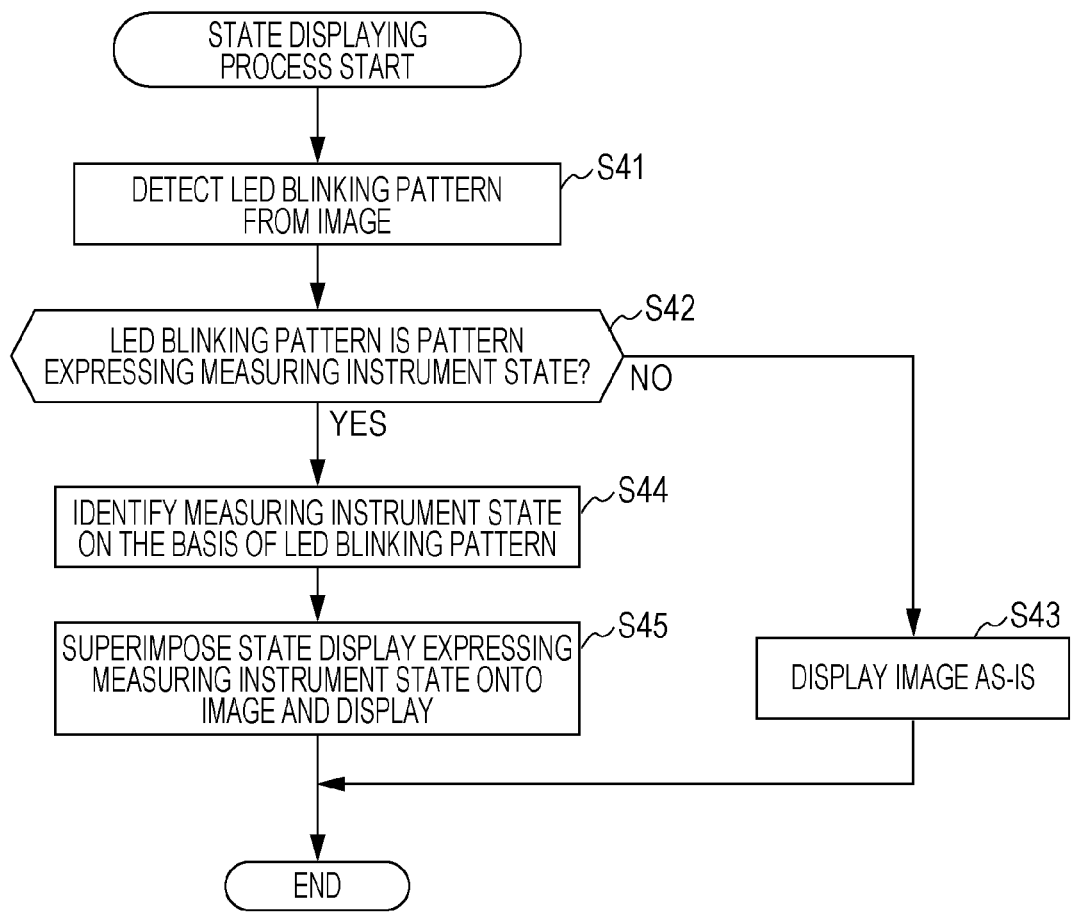
FIG. 5 is a flowchart for illustrating a state displaying process conducted by the smartphone in FIG. 4.
Figure 9:
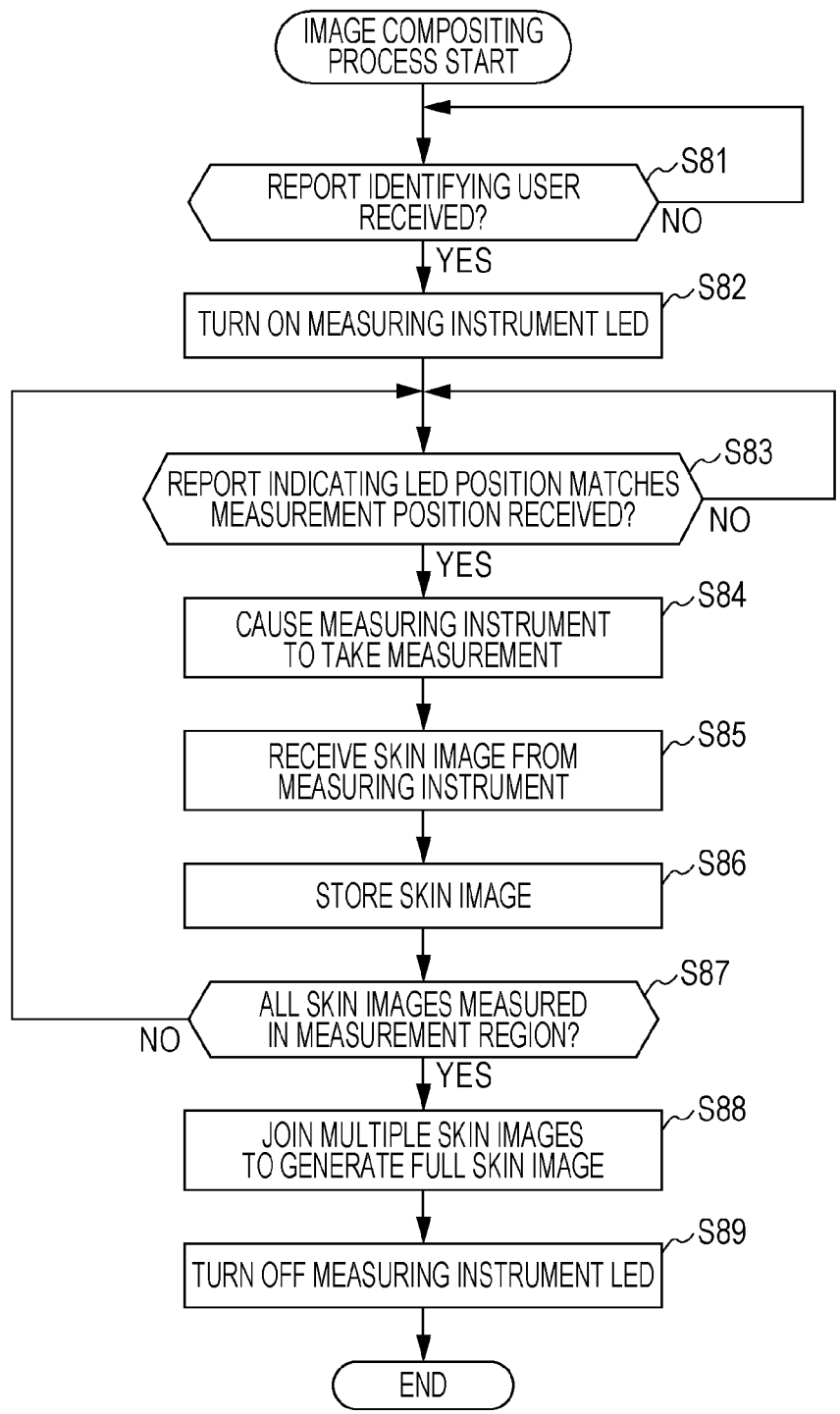
FIG. 9 is a flowchart for illustrating an image compositing process conducted by the smartphone in FIG. 6.

Note that the smartphone 22 may be configured to activate an application that conducts processes such as the reporting process in FIG. 3, the state displaying process in FIG. 5, the measurement controlling process in FIG. 7, and the image compositing process in FIG. 9 in response to the measuring instrument 21' being detached.

Figure 11:
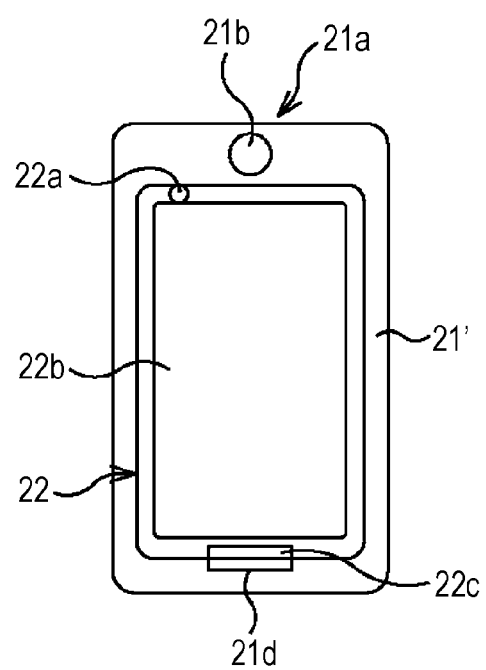
FIG. 11 is a diagram illustrating an example of a jacket-style measuring instrument attached to a smartphone.

Next, FIG. 11 illustrates an example of when the measuring instrument 21' is attached to the smartphone 22.

When the measuring instrument 21' is attached to the smartphone 22, the charging connector 21d of the measuring instrument 21' physically connects to a power supply connector 22c of the smartphone 22, as illustrated in FIG. 11.

The power supply connector 22c is a connector provided to supply power to the measuring instrument 21', and supplies power to the physically connected charging connector 21d from a power supply (not illustrated) in the smartphone 22.

Note that in the smartphone 22, the power supply (not illustrated) supplies the power supply connector 22c with at least one of power from a battery (not illustrated) in the smartphone 22, or power from a charger used to charge the smartphone 22.

The charging connector 21d charges a battery (not illustrated) built into the measuring instrument 21' by supplying power from the power supply connector 22c.

In the case of adopting a jacket-style measuring instrument 21' that is freely attachable to and detachable from the smartphone 22 as illustrated in FIG. 11, a user leaving home while carrying the smartphone 22 will naturally also bring the measuring instrument 21', thereby making it possible to prevent situations where the user forgets the measuring instrument 21' at home, for example.

Thus, the user is able to use the measuring instrument 21' to perform fixed point observation of his or her skin even when away from home.

Furthermore, since the measuring instrument 21' is configured to be attached to the smartphone 22 in an integrated way, a user is able to bring along the measuring instrument 21' and the smartphone 22 without feeling relatively burdened.

In addition, the smartphone 22 is used to take skin measurements in addition to sending and receiving email and using the phone. For this reason, the user is freed from taking a device separate from the smartphone 22, such as a special-purpose display device that displays an image obtained by imaging the user and the LED 21b, away from home.

Furthermore, since the measuring instrument 21' is charged by the power supply (not illustrated) built into the smartphone 22 when the measuring instrument 21' is attached to the smartphone 22, it is possible to avoid situations where the battery in the measuring instrument 21' runs out while away from home.

Thus, it becomes possible to avoid situations where the user becomes unable to take a skin data measurement because the battery in the measuring instrument 21' has run out.

Note that if the user uses a mirror when taking a skin data measurement with the measuring instrument 21', it is possible to perform fixed point observation of skin data even with the measuring instrument 21' still attached to the smartphone 22.

Figure 12:
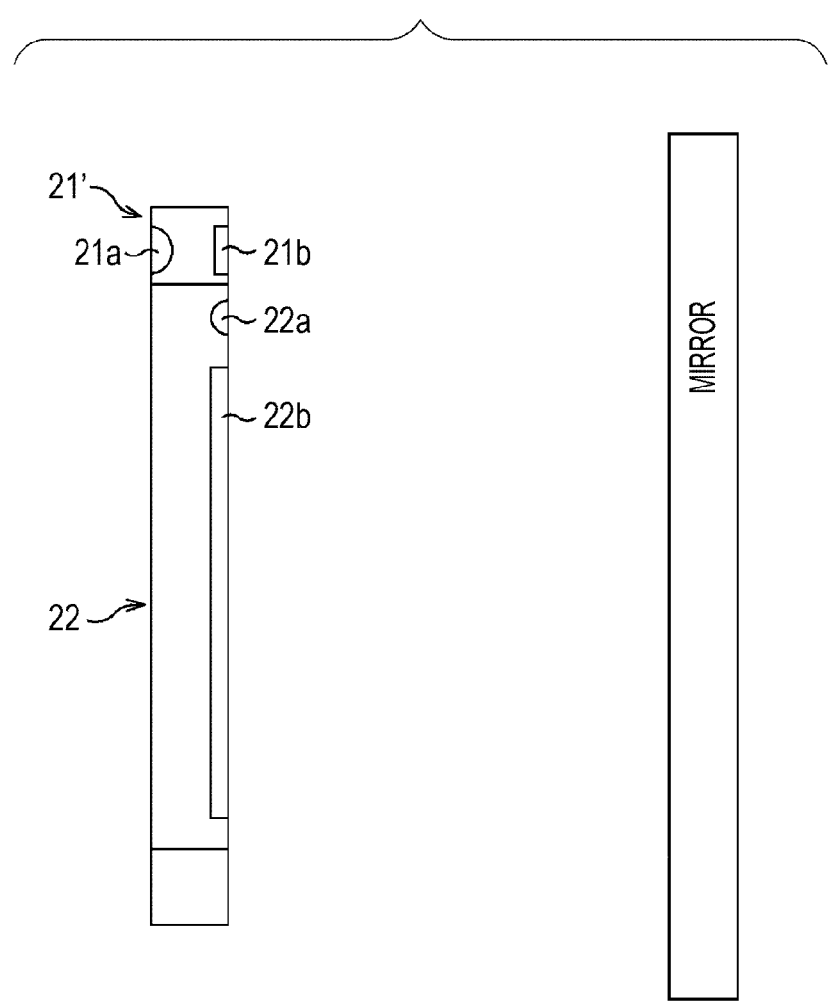
FIG. 12 is a diagram illustrating an example of causing a jacket-style measuring instrument to measure skin data while attached to a smartphone.

Next, FIG. 12 illustrates an example of causing the jacket-style measuring instrument 21' to measure skin data with the measuring instrument 21' still attached to the smartphone 22.

In the case of causing the measuring instrument 21' to take a measurement with the measuring instrument 21' still attached to the smartphone 22, the user moves the measuring instrument 21' in close proximity to his or her face while referring to content displayed on the LCD 22b and reflected in the mirror.

Thus, the user is able to refer to content displayed on the LCD 22b of the smartphone 22 (such as an image obtained from imaging by the imaging unit 22a, for example) via the mirror in front of the user, similarly to the case of the measuring system 1 in FIG. 1.

Also, the imaging unit 22a built into the smartphone 22 is able to obtain an image similar to the case in FIG. 1 by imaging the user reflected in the mirror as well as the LED 21b of the measuring instrument 21' likewise reflected in the mirror.

Note that even in the case of another measuring instrument in which the positions of the camera 21a and the LED 21b are the reverse of the measuring instrument 21' illustrated in FIG. 12, a driving unit able to change the positions of the camera 21a and the LED 21b to positions like those illustrated in FIG. 12 may be provided.

In this case, the other measuring instrument is able to take a skin measurement while still attached to the smartphone 22.

Note that even in the case of inseparably providing the smartphone 22 with the measuring instrument 21, such a smartphone 22 may still be used to take a skin measurement as described with reference to FIG. 12.

Also, the smartphone 22 may be utilized for other uses besides measuring skin data while the measuring instrument 21' is attached.

Example of Use as Magnifying Glass

Figure 13:
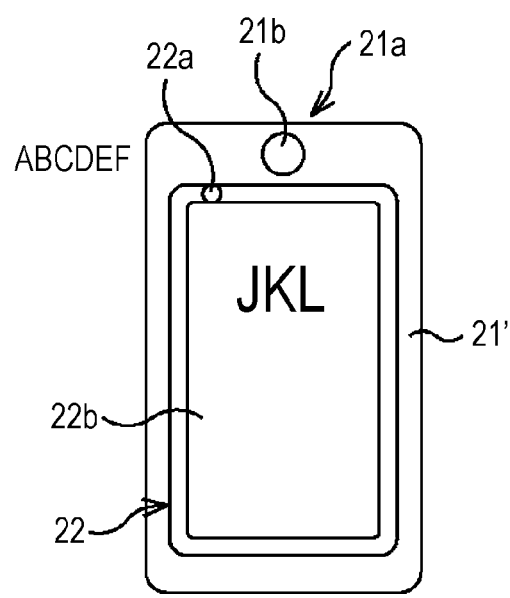
FIG. 13 is a diagram illustrating an example of using a measuring instrument and a smartphone as a magnifying glass.

Next, FIG. 13 illustrates an example of using the measuring instrument 21' and the smartphone 22 as a magnifying glass.

FIG. 13 illustrates the smartphone 22 displaying an enlarged view of the letters "JKL" from among the letters "ABCDEFGHIJKLMNO" on the LCD 22b.

Note that FIG. 13 illustrates a state in which only the letters "ABCDEF" from among the letters "ABCDEFGHI-JKLMNO" are visible, with the remaining letters "GHI-JKLMNO" hidden by the measuring instrument 21' and the smartphone 22.

In FIG. 13, the measuring instrument 21' uses the built-in camera 21a to take a close-up image of the area showing the letters "JKL", and supplies an image obtained by such imaging to the smartphone 22.

The smartphone 22 then enlarges the image from the measuring instrument 21' and displays the enlarged image on the LCD 22b.

Thus, the measuring instrument 21' and the smartphone 22 can be used as a magnifying glass, as illustrated in FIG. 12.

Note that the measuring instrument 21' and the smartphone 22 can be used as a magnifying glass even when the measuring instrument 21' is detached from the smartphone 22. In this case, the measuring instrument 21' transmits an image obtained from imaging by the built-in camera 21a to the smartphone 22 by wireless communication, for example.

The smartphone 22 may also execute an application for functioning as a magnifying glass in the case where the measuring instrument 21' is attached, and execute an application for taking a skin measurement in the case where the measuring instrument 21' is detached, for example.

Figure 14:
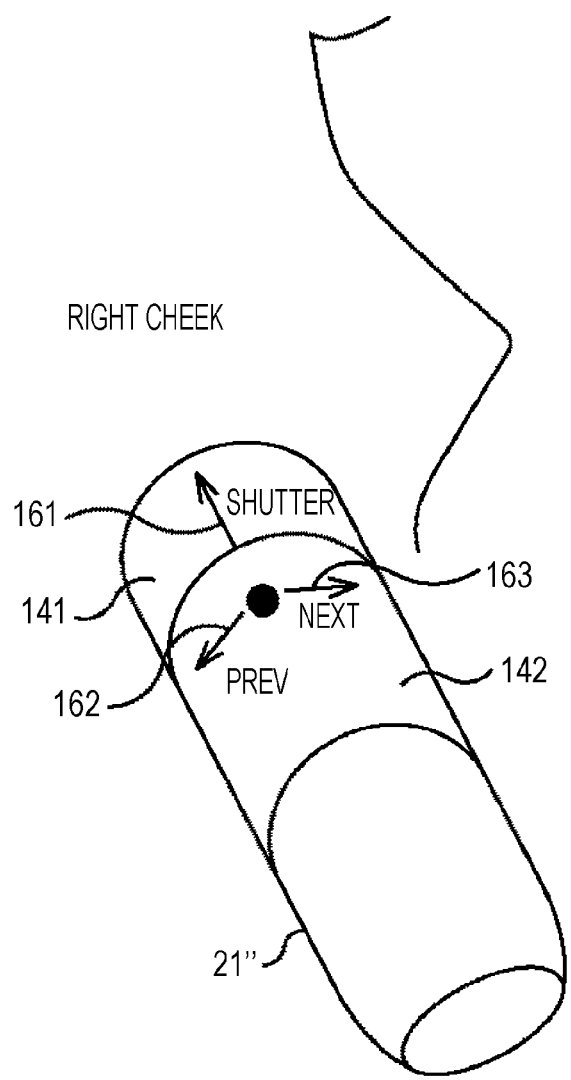
FIG. 14 is a diagram illustrating an example of a measuring instrument with improved usability.

Next, FIG. 14 illustrates an example of a measuring instrument 21" with improved usability.

As illustrated in FIG. 14, the measuring instrument 21" has a cylindrical shape, and includes a lens barrel 141 and a mode switcher 142, for example. Note that although the measuring instrument 21' is provided with components such as the camera 21a and the LED 21b similarly to the measuring instrument 21, these components are omitted from illustration to avoid complication in the drawings.

The lens barrel 141 is a cylindrical portion surrounding components such as the optics of the camera 21a, and is set to either an OFF state or an ON state, for example. In addition, the lens barrel 141 switches from the OFF state to the ON state when depressed by the skin imaged with the camera 21a.

In other words, in the case where the measuring instrument 21' is pushed in the direction of the arrow 161 illustrated in FIG. 14, for example, the lens barrel 141 of the measuring instrument 21" is depressed by an area on the user's face (for example, the right cheek in FIG. 14), and switches to the ON state.

In this case, in response to the lens barrel 141 switching to the ON state, for example, the camera 21a takes an image of the skin pressing against the measuring instrument 21" (for example, the right cheek in FIG. 14). In other words, the lens barrel 141 functions as a shutter button for the camera 21a, switching from the OFF state to the ON state when the taking an image with the camera 21a, for example.

Herein, since the direction of the arrow 161 and the imaging direction (optical axis) of the camera 21a are the same direction, image shake (almost) might not occur when taking an image with the camera 21a.

Consequently, the measuring instrument 21" is capable of taking clear skin images without shake.

The mode switcher 142 is freely rotatable about the optical axis of the camera 21a in the directions of the arrow 162 and the arrow 163 illustrated in FIG. 14, and is operated when switching among various operating modes of the measuring instrument 21".

In other words, if the mode switcher 142 is rotated in the direction of the arrow 162, for example, the operating mode of the measuring instrument 21" is switched to the previous operating mode. Also, if the mode switcher 142 is rotated in the direction of the arrow 163, for example, the operating mode of the measuring instrument 21" is switched to the next operating mode.

Specifically, a first operating mode, a second operating mode, and a third operating mode may exist, for example, and in the case where the measuring instrument 21" is in the second operating mode, the operating mode is switched as follows according to a user switching operation.

Namely, the user is able to simply rotate the mode switcher 142 in the direction of the arrow 162 to switch the measuring instrument 21" from the second operating mode to the first operating mode.

As another example, the user is able to simply rotate the mode switcher 142 in the direction of the arrow 163 to switch the measuring instrument 21" from the second operating mode to the third operating mode.

Thus, the user becomes able to easily switch operating modes without feeling burdened compared to the case of switching the operating mode of the measuring instrument 21" by operating the smartphone 22, for example.

As another example, since the user is able to switch the operating mode of the measuring instrument 21" without operating the smartphone 22, it is possible to prevent a situation where the user is distracted by operating the smartphone 22 and drops the measuring instrument 21".

Note that modes such as an operating mode when measuring skin on the left cheek and an operating mode when measuring skin on the right cheek may be adopted as operating modes of the measuring instrument 21", for example.

As another example, by linking to software on the smartphone 22, the measuring instrument 21" is able to select and confirm items displayed on the LCD 22b of the smartphone 22 in response to operations by the user.

In other words, if the user rotates the mode switcher 142 in the direction of the arrow 162 on the measuring instrument 21', the previous item is selected by a cursor, for example. Also, if the user rotates the mode switcher 142 in the direction of the arrow 163, the next item is selected by a cursor, for example.

If the user then pushes the measuring instrument 21" in the direction of the arrow 161, the lens barrel 141 of the measuring instrument 21" is depressed. In so doing, the item currently selected by the cursor on the smartphone 22 is confirmed, and a display corresponding to the confirmed item is displayed on the LCD 22b.

Note that in the measuring system 1 in FIG. 1, the LCD 22b of the smartphone 22 displays an image obtained from imaging by the imaging unit 22a, for example.

However, in addition to displaying images that have already been taken, the LCD 22b may also display a skin image obtained by the camera 21a built into the measuring instrument 21 as a through-the-lens image used to determine photographic composition.

In this case, the measuring instrument 21 uses wireless communication or the like to supply the smartphone 22 with a skin image obtained from the camera 21a as a through-the-lens image. This applies similarly to the case of using the measuring instrument 21' or the measuring instrument 21" instead of the measuring instrument 21 in FIG. 1.

As another example, although the measuring system 1 is made up of a measuring instrument 21 and a smartphone 22, a device such as a tablet or personal computer may also be adopted instead of the smartphone 22.

Meanwhile, the present technology may take the following configurations.

(1) A method of performing a fixed point observation comprising: receiving an image comprising a user and a measuring unit; determining a position of the measuring unit based on the received image; retrieving a stored measurement position associated with the measuring unit; determining if the retrieved measurement position associated with the measuring unit matches the determined position of the measuring unit; and providing an indication that the retrieved measurement position associated with the measuring unit matches the determined position of the measuring unit.

(2) The method of (1), further comprising: identifying the user based on the received image, wherein retrieving a stored measurement position further comprises retrieving a measurement position associated with the identified user.

(3) The method of (1), wherein the position of the measuring unit is determined by calculating a position of a marker associated with the measuring unit.

(4) The method of (3), wherein the marker is a light emitter that blinks in a predetermined blinking pattern by turning on and off, the method further comprising detecting the blinking pattern of the marker on the basis of whether the marker is on or off in the image.

(5) The method of (1), further comprising displaying an image comprising an image of the user and an image of the measuring unit to an imaging unit display.

(6) The method of (1), further comprising:
in response to the indication that the retrieved measurement position associated with the measuring unit matches the determined position of the measuring unit, acquiring measurement data from the measurement unit.

(7) The method of (1), wherein the image is acquired at an imaging unit; and wherein the position of the measuring unit is based on a position of an LED associated with the measuring unit.

(8) The method of (7), further comprising: acquiring skin measurement data using the measurement unit.

(9) The method of (8), wherein the measuring unit measures the user's skin by taking an image in close proximity and further generating, on the basis of a plurality of skin images obtained from the measurement unit, a full skin image formed by joining the plurality of skin images together.

(10) The method of (1), further comprising: identifying a state associated with the measuring unit, the state of the measuring unit comprising at least one of on and off; and displaying the state of the measuring unit and at least one image.

(11) The method of (1), further comprising: storing the determined position of the measuring unit as a new measurement position; receiving a second image comprising the user and the measuring unit; determining the position of the measuring unit based on the received image; retrieving the new measurement position; determining if the retrieved new measurement position of the measuring unit matches the determined position of the measuring unit; and providing an indication that the retrieved new measurement position of the measuring unit matches the determined position of the measuring unit.

(12) The method of (1), further comprising:
receiving depth information indicating positions in a depth direction; receiving measurement information from the measurement unit, the measurement information comprising skin image data; and generating a three-dimensional image map based on the received depth information and the received measurement information.

(13) The method of (1), further comprising: receiving measurement information corresponding to different wavelengths of light.

(14) A measuring system for performing a fixed point observation comprising: an imaging unit comprising at least one image sensor; a measuring instrument including at least one marker; a position computing unit; a determining unit; and an output controller; wherein the imaging unit is configured to acquire an image comprising a user and the marker, and provide the acquired image to the position computing unit; wherein the position computing unit is configured to compute a position of the marker with respect to the user based on the image provided by the imaging unit, and further provide the computed position to the determining unit; wherein the determining unit is configured to determine whether the computed position of the marker matches a retrieved measurement position, and further output the result of the determination to the output controller; and wherein the output controller is configured to provide an indication when the marker position matches the measurement position.

(15) The measuring system of (14), further comprising:

a user identifying unit configured to receive an image from the imaging unit, detect one or more features associated with the user, and identify a user based on the detected one or more features; wherein the retrieved measurement position is a measurement position associated with the identified user.

(16) The measuring system of (14), wherein the marker is an LED that emits at least one of visible light, ultraviolet light and infrared light.

(17) The measuring system of (14), wherein the marker is a light emitter that blinks in a predetermined blinking pattern by turning on and off, and the measuring system further comprises a pattern detector that detects the blinking pattern of the marker on the basis of whether the marker is on or off in the image.

(18) The measuring system of (17), wherein the measuring instrument is further configured to acquire measurement data in response to the retrieved measurement position matching the computed position of the LED.

(19) The measuring system of (18), wherein the measurement data comprises skin measurement data.

(20) The measuring system of (19), further comprising:

wherein the measuring instrument measures the user's skin by taking an image in close proximity; and the measuring system further comprises: a generator that, on the basis of a plurality of skin images obtained from the measurement unit, generates a full skin image formed by joining the plurality of skin images together.

(21) The measuring system of (14), further comprising an irradiating unit configured to successively emit light at different wavelengths; wherein the measuring instrument acquires measurement data for each successive light emission.

(22) The measuring system of (14), further comprising: acquiring skin measurement data utilizing the measurement instrument.

(23) The measuring system of (14), wherein the measuring instrument is freely attachable to and detachable from the imaging unit.

(24) The measuring system of (14), further comprising:

an orientation identifying unit that identifies the orientation of the measuring instrument.

(25) The measuring system of (24), wherein the measuring instrument includes a sensor that senses the motion of the measuring instrument, and the orientation identifying unit identifies the orientation of the measuring instrument on the basis of the sensing results from the sensor.

(26) The measuring system of (25), wherein the marker is a graphical figure provided on a case of the measuring instrument; and the orientation identifying unit identifies the orientation of the measuring instrument on the basis of the shape of the graphical figure in the image.

(27) A method of performing a fixed point observation comprising: determining a position of a measuring instrument based on an image of the measuring instrument; and initiating a measurement by the measuring instrument when the position of the measuring instrument matches a retrieved measurement position.

(28) The method of performing a fixed point observation according to (27), wherein the measurement by the measuring instrument is skin measurement data.

(29) The method of performing a fixed point observation according to (27), wherein the determined position of the measuring instrument is based on a position of the measuring instrument in an image in relation to a user in the image.

(30) An information processing apparatus including:

an imaging unit that takes an image of a subject, together with a marker provided on a measuring instrument that measures part of the subject while in close proximity;

a position computing unit that computes a marker position expressing the position of the marker with respect to the subject, on the basis of the image obtained from the imaging by the imaging unit; and a controller that conducts a predetermined controlling process in the case where the marker position matches a measurement position, the measurement position being the marker position when measuring part of the subject.

(31) The information processing apparatus according to (30), wherein the marker is a light emitter that blinks in a predetermined blinking pattern by turning on and off, and the information processing apparatus further includes:

a pattern detector that detects the blinking pattern of the marker on the basis of whether the marker is on or off in the image.

(32) The information processing apparatus according to (31), wherein the marker blinks in a blinking pattern expressing the state of the measuring instrument, and the information processing apparatus further includes:

a display controller that causes a display to display the state of the measuring instrument on the basis of the detection result from the pattern detector.

(33) The information processing apparatus according to (30) to (32), wherein the controller conducts the predetermined controlling process every time the marker position matches respective measurement positions on a track traced as the measuring instrument moves.

(34) The information processing apparatus according to (30) to (33), wherein in the case where the marker position matches a measurement position, the controller conducts at least one of a first controlling process that reports the match to the user, and a second controlling process that controls the measuring instrument and causes the measuring instrument to measure part of the subject.

(35) The information processing apparatus according to (30) to (34), further including:

an orientation identifying unit that identifies the orientation of the measuring instrument.

(36) The information processing apparatus according to (35), wherein
the measuring instrument includes a sensor that senses the motion of the measuring instrument, and
the orientation identifying unit identifies the orientation of the measuring instrument on the basis of the sensing results from the sensor.

(37) The information processing apparatus according to (35), wherein
the marker is a graphical figure provided on the case of the measuring instrument, and
the orientation identifying unit identifies the orientation of the measuring instrument on the basis of the shape of the graphical figure in the image.

(38) The information processing apparatus according to (30) to (34),
wherein the measuring instrument measures the subject's skin by taking an image in close proximity,
the information processing apparatus further including:
a generator that, on the basis of a plurality of skin images obtained from imaging by the measuring instrument, generates a full skin image formed by joining the plurality of skin images together.

(39) The information processing apparatus according to (38), further including:
a distance measuring unit that measures the distances to the measurement positions; and
a three-dimensional position computing unit that computes the three-dimensional positions of the skin images on the basis of the measurement positions and the distances;
wherein the generator generates a full skin image stereoscopically displaying the subject's skin additionally on the basis of the three-dimensional positions of the plurality of skin images.

(40) The information processing apparatus according to (30) to (34), wherein the measuring instrument includes
an irradiating unit that irradiates part of the subject with light at a plurality of different wavelengths, and
a camera measuring unit that measures part of the subject by taking an image of skin being irradiated with light at a particular wavelength for each of the plurality of different wavelengths.

(41) The information processing apparatus according to (30) to (34), wherein
the measuring instrument is freely attachable to and detachable from the information processing apparatus.

(42) The information processing apparatus according to (41), wherein
the measuring instrument is capable of being electrically recharged while attached to the information processing apparatus.

(43) The information processing apparatus according to (30) to (34), wherein the measuring instrument includes
a camera measuring unit that takes a close-up image of part of the subject,
a lens barrel, having a cylindrical shape surrounding the camera measuring unit, and configured to switch on when pushed against part of the subject, and
a rotary unit that rotates about the optical axis of the camera measuring unit according to a rotating operation by the user.

(44) The information processing apparatus according to (43), wherein
the camera measuring unit takes a close-up image of part of the subject when the lens barrel is switched on, and
the rotary unit rotates about the optical axis of the camera measuring unit when switching operating modes related to the operation of the camera measuring unit.

(45) An information processing method conducted by an information processing apparatus including an imaging unit that takes an image of a subject, together with a marker provided on a measuring instrument that measures part of the subject while in close proximity, the information processing method including:
computing a marker position expressing the position of the marker with respect to the subject, on the basis of the image obtained from the imaging by the imaging unit; and
conducting a predetermined controlling process in the case where the marker position matches a measurement position, the measurement position being the marker position when measuring part of the subject.

(46) A program executed by a computer in an information processing apparatus including an imaging unit that takes an image of a subject, together with a marker provided on a measuring instrument that measures part of the subject while in close proximity, the program causing the computer to function as:
a position computing unit that computes a marker position expressing the position of the marker with respect to the subject, on the basis of the image obtained from the imaging by the imaging unit; and
a controller that conducts a predetermined controlling process in the case where the marker position matches a measurement position, the measurement position being the marker position when measuring part of the subject.

(47) A measuring system including:
a measuring instrument that takes a measurement while in close proximity to a user; and
an information processing apparatus including an imaging unit that takes an image of the user and the measuring instrument; wherein the measuring instrument includes
a measuring unit that measures part of the user while in close proximity, and
a marker provided on the case of the measuring instrument, and the information processing apparatus includes
an imaging unit that takes an image of the user, together with the marker provided on the measuring instrument,
a position computing unit that computes a marker position expressing the position of the marker with respect to the user, on the basis of the image obtained from the imaging by the imaging unit, and
a controller that conducts a predetermined controlling process in the case where the marker position matches a measurement position, the measurement position being the marker position when measuring part of the user.

The foregoing series of processing operations may be executed in hardware, and may also be executed in software, for example. In the case of executing the series of processing operations in software, a program constituting such software may be installed from a program recording medium onto a computer built into special-purpose hardware, or alternatively, onto a computer capable of executing various functions by installing various programs thereon, such as a general-purpose personal computer, for example.

<Exemplary Configuration of Computer>

Figure 15:
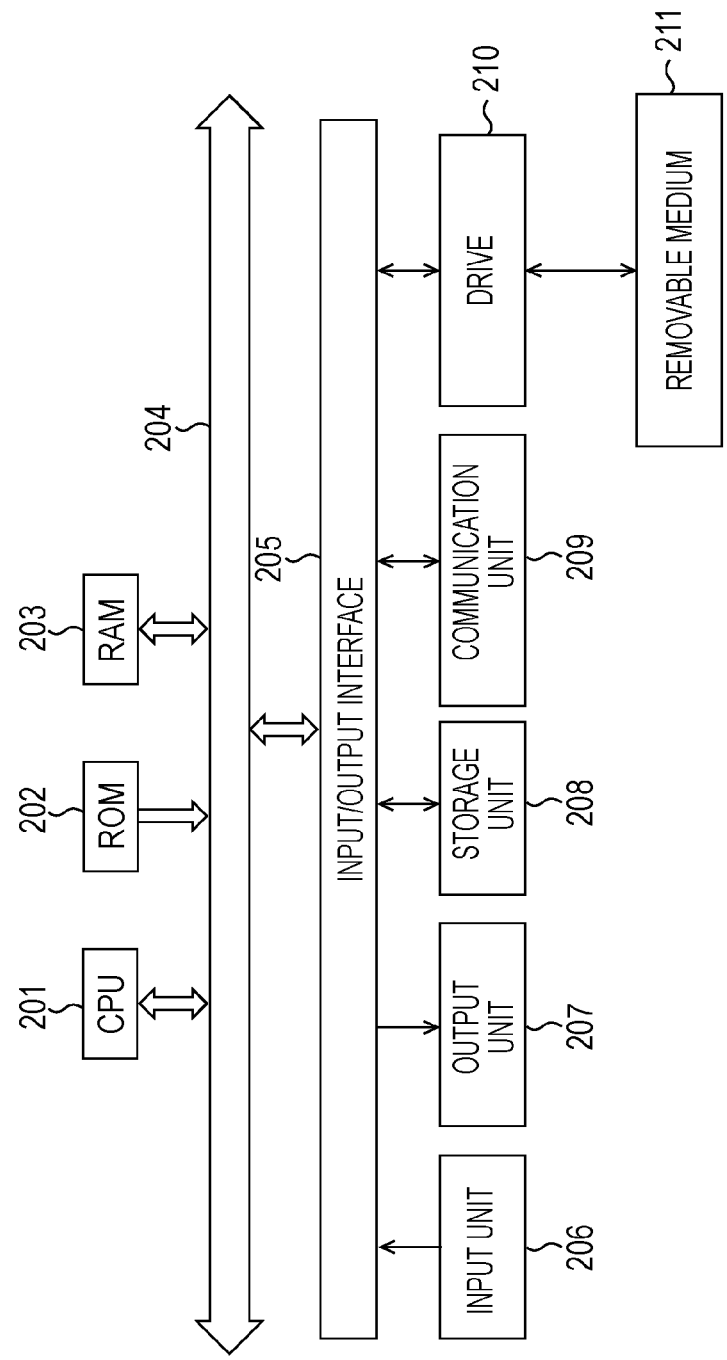
FIG. 15 is a block diagram illustrating an exemplary hardware configuration of a computer.

FIG. 15 illustrates an exemplary hardware configuration of a computer that executes the foregoing series of processing operations according to a program.

A central processing unit (CPU) 201 executes various processing operations according to a program stored in read-only memory (ROM) 202 or a storage unit 208. Random access memory (RAM) 203 stores information such as programs executed by the CPU 201 and data as appropriate. The CPU 201, the ROM 202, and RAM 203 are connected to each other by a bus 204.

Additionally, an input/output interface 205 is connected to the CPU 201 via the bus 204. Connected to the input/output interface 205 are an input unit 206 which includes devices such as a keyboard, mouse, and microphone, and an output unit 207 which includes devices such as a display and one or more speakers. The CPU 201 executes various processing operations in response to commands input from the input unit 206. The CPU 201 then outputs processing results to the output unit 207.

A storage unit 208 connected to the input/output interface 205 includes a hard disk, for example, and stores programs executed by the CPU 201 and various data. A communication unit 209 communicates with external devices via a network such as the Internet or a local area network.

Programs may also be acquired via the communication unit 209 and stored in the storage unit 208.

A drive 210 connected to the input/output interface 205 drives an inserted removable medium 211 such as a magnetic disk, an optical disc, a magneto-optical disc, or semiconductor memory, and acquires information such as programs and data recorded thereon. Acquired programs and data are transferred to the storage unit 208 and stored as appropriate.

As illustrated in FIG. 15, a recording medium that records (stores) a program to be installed onto a computer in a computer-executable state may be a removable medium 211 as an instance of packaged media such as magnetic disks (including flexible disks), optical discs (including Compact Disc-Read-Only Memory (CD-ROM) and Digital Versatile Disc (DVD)), magneto-optical discs (including Mini-Disc (MD)), or semiconductor memory. Alternatively, such a recording medium may be the ROM 202 in which the program is transiently or permanently stored, or the hard disk constituting the storage unit 208. The recording of the program to the recording medium is conducted using a wired or wireless communication medium such as a local area network, the Internet, or digital satellite broadcasting via the communication unit 209, which may be a router, modem, or other interface as appropriate.

Note that, in this specification, the steps describing the foregoing series of processing operations obviously encompass processing operations conducted in a time series following the stated order, but also encompass operations executed in parallel or individually without strictly being processed in a time series.

Also, in this specification, the term "system" denotes the totality of an apparatus composed of multiple apparatus.

Furthermore, the present disclosure is not limited to the foregoing embodiments, and various modifications are possible within a scope that does not depart from the principal matter of the present disclosure.

The present disclosure contains subject matter related to that disclosed in Japanese Priority Patent Application JP 2012-206838 filed in the Japan Patent Office on Sep. 20, 2012, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Measuring system
21, 21', 21" Measuring instrument
21a Camera
21b LED
21c Communication unit
21d Charging connector
22 Smartphone
22a Imaging unit
22b LCD
22c Power supply connector
41 Optics
42 Image sensor
43 Signal processing IC
61 User identifying unit
62 Position computing unit
63 Determining unit
63a Memory
64 Output controller
65 Speaker
66 Display controller
67 Main controller
68 Operable unit
81 Pattern detector
82 State identifying unit
83 Display controller
101 Communication controller
102 Communication unit
103 Data storage unit
141 Lens barrel
142 Mode switcher

What is claimed is:

1. A measuring system for performing a fixed point observation comprising:
an imaging unit comprising at least one image sensor;
a measuring instrument including a marker;
a position computing unit;
a determining unit; and
an output controller;
wherein the imaging unit is configured to acquire an image including at least a portion of a user and the marker, and provide the acquired image to the position computing unit;
wherein the position computing unit is configured to compute a position of the marker with respect to the user based on the image provided by the imaging unit, and further provide the computed position to the determining unit;
wherein the determining unit is configured to determine whether the computed position of the marker matches a retrieved measurement position, and further output a result of the determination to the output controller; and
wherein the output controller is configured to provide an indication when the marker position matches the measurement position.

2. The measuring system of claim 1, further comprising:
a user identifying unit configured to receive an image from the imaging unit, detect one or more features associated with the user, and identify the user based on the detected one or more features,
wherein the retrieved measurement position is a measurement position associated with the identified user.

3. The measuring system of claim 1, wherein the marker is an LED that emits at least one of visible light, ultraviolet light and infrared light.

4. The measuring system of claim 1, wherein the marker is a light emitter that blinks in a predetermined blinking pattern by turning on and off, and the measuring system further comprises a pattern detector that detects the blinking pattern of the marker on the basis of whether the marker is on or off in the image.

5. The measuring system of claim 4, wherein the measuring instrument is further configured to acquire measurement data in response to the retrieved measurement position matching the computed position of an LED.

6. The measuring system of claim 5, wherein the measurement data comprises skin measurement data.

7. The measuring system of claim 6, wherein the measuring instrument measures skin of the user by taking an image in close proximity; and the measuring system further comprises a generator that, on the basis of a plurality of skin images obtained from the measurement instrument, generates a full skin image formed by joining the plurality of skin images together.

8. The measuring system of claim 1, further comprising an irradiating unit configured to successively emit light at different wavelengths, wherein the measuring instrument acquires measurement data for each successive light emission.

9. The measuring system of claim 1, further comprising: acquiring skin measurement data utilizing the measurement instrument.

10. The measuring system of claim 1, wherein the measuring instrument is freely attachable to and detachable from the imaging unit.

11. The measuring system of claim 1, further comprising: an orientation identifying unit that identifies an orientation of the measuring instrument.

12. The measuring system of claim 11, wherein the measuring instrument includes a sensor that senses a motion of the measuring instrument, and the orientation identifying unit identifies the orientation of the measuring instrument on the basis of sensing results from the sensor.

13. The measuring system of claim 12, wherein the marker is a graphical figure provided on a case of the measuring instrument; and the orientation identifying unit identifies the orientation of the measuring instrument on the basis of a shape of the graphical figure in the image.

* * * * *